US010111909B2

(12) United States Patent
Vesey et al.

(10) Patent No.: US 10,111,909 B2
(45) Date of Patent: Oct. 30, 2018

(54) THERAPEUTICS USING ADIPOSE CELLS AND CELL SECRETIONS

(71) Applicant: Cell Ideas Pty Ltd, Gordon, NSW (AU)

(72) Inventors: Graham Vesey, Hornsby (AU); Rebecca Anne Webster, Avalon (AU); Richard Lilischkis, Westleigh (AU)

(73) Assignee: Cell Ideas Pty Ltd, Gordon, NSW (AU)

( * ) Notice: Subject to any disclaimer, the term of this patent is extended or adjusted under 35 U.S.C. 154(b) by 0 days.

(21) Appl. No.: 14/342,479

(22) PCT Filed: Sep. 21, 2012

(86) PCT No.: PCT/AU2012/001140
§ 371 (c)(1),
(2) Date: Mar. 3, 2014

(87) PCT Pub. No.: WO2013/040649
PCT Pub. Date: Mar. 28, 2013

(65) Prior Publication Data
US 2014/0234272 A1    Aug. 21, 2014

(30) Foreign Application Priority Data

Sep. 23, 2011  (AU) ................ 2011903938
Apr. 4, 2012   (AU) ................ 2012901350
Aug. 23, 2012  (AU) ................ 2012903646

(51) Int. Cl.
*A61K 35/28*   (2015.01)
*A61K 35/35*   (2015.01)
*A01N 1/02*    (2006.01)

(52) U.S. Cl.
CPC ............ *A61K 35/35* (2013.01); *A01N 1/0221* (2013.01); *A61K 35/28* (2013.01)

(58) Field of Classification Search
CPC .... C12N 5/0653; C12N 5/0666; A61K 35/35; A61K 35/28; A01N 1/02; A01N 1/0205; A01N 1/021; A01N 1/0221; A01N 1/0226
See application file for complete search history.

(56) References Cited

U.S. PATENT DOCUMENTS

| | | | |
|---|---|---|---|
| 6,037,175 A | 3/2000 | Cameron et al. | |
| 2006/0018887 A1* | 1/2006 | Kadiyala | A61K 35/32 424/93.7 |
| 2006/0228796 A1* | 10/2006 | Kolkin et al. | 435/325 |
| 2007/0036768 A1* | 2/2007 | Fraser | C12N 5/0667 424/93.7 |
| 2010/0092432 A1 | 4/2010 | Ozaki et al. | |
| 2011/0268708 A1† | 11/2011 | Lin | |

FOREIGN PATENT DOCUMENTS

| | | |
|---|---|---|
| WO | 2003/024215 A1 | 3/2003 |
| WO | 2003/040346 A2 | 5/2003 |
| WO | 2005/035742 A2 | 4/2005 |
| WO | 2003/053346 A2 | 8/2006 |
| WO | 08/060374 A2 | 5/2008 |
| WO | 2009/115581 A2 | 9/2009 |
| WO | 10/020005 A1 | 2/2010 |
| WO | 2010/020005 A1 † | 2/2010 |
| WO | 11/047345 A2 | 4/2011 |

OTHER PUBLICATIONS

Zhang et al, Journal of Endocrinology, 2000, vol. 164, pp. 119-128.*
Yoshimura et al, "Characterization of Freshly Isolated and Cultured Cells Derived from the Fatty and Fluid Portions of Liposuction Aspirates" Journal of Cellular Physiology, 2006, vol. 208, pp. 64-76. (Year: 2006).*
Rossi et al., "Intravenous human adipose stem cells reverse neuropathic pain symptoms and restore pro-anti infammatory cytokine balance in the chronic constriction injury murine model", Societa Italiana Di Farmacologia, 35 Congresso Nazionale, Sep. 14-17, 2011, 1 page.
Mosna et al., "Human Bone Marrow and Adipose Tissue Mesenchymal Stem Cells: A Users Guide", Stem Cells and Development, 2010, 19(10), 1449-1470.
Cryopreservation of Mammalian Cells [retrieved on Nov. 27, 2012] Retrieved from internet URL: http://web.archive.org/web/20100731020103/http://www.invitrogen.com/site/us/en/home/References/gibco-cell-culture-basics/cell-culture-protocols/cryopreservation-of-mammalian-cells.html; published Jul. 31, 2010 as per Wayback Machine Whole document, 2 pages.
Siniscalco et al., "Long-lasting effects of human mesenchymal stem cell systemic administration on pain-like behaviors, cellular, and biomolecular modifications in neuropathic mice", Frontiers in Integrative Neuroscience, 2011, vol. 5, Article 79, 1-10.
Blaber, S.P. et al., "Analysis of in vitro secretion profiles from adipose-derived cell populations," Journal of Translational Medicine 10:172 (2012).
Cui, X.D., et al., "Cryopreservation of human adipose tissues," Cryobiology, 55:269 (2007).
Ji, L, et al. "Cryopreservation of Adherent Human Embryonic Stem Cells," Biotechnology and Bioengineering, 88:299 (2004).
Koliakos, I, et al., "Mesenchymal cells isolation from Wharton's jelly, in perspective to clinical applications," Journal of Biological Research—Thessaloniki 16: 194-201 (2011).
Salgado, A.J., et al., "Adipose Tissue Derived Stem Cells Secretome: Soluble Factors and Their Roles in Regenerative Medicine," Current Stem Cell Research & Therapy, 5:103-110 (2010).
Pak, J., "Regeneration of human bones in hip osteonecrosis and human cartilage in knee osteoarthritis with autologous adipose-tissue-derived stem cells: a case series," Journal of Medical Case Reports 5:296 (2011).

(Continued)

*Primary Examiner* — Allison M Fox
(74) *Attorney, Agent, or Firm* — McDonnell Boehnen Hulbert & Berghoff LLP

(57) ABSTRACT

The invention relates to compositions comprising (i) adipose tissue-derived cell secretions or (ii) an adipose tissue-derived cell suspension, optionally comprising adipocytes, or (iii) a combination of adipose tissue-derived cell secretions and an adipose tissue-derived cell suspension, optionally comprising adipocytes, and to their use in pharmaceutical compositions and methods for treatment of various conditions. The invention also relates to improved methods, agents and compositions for cryopreservation of cells.

18 Claims, 6 Drawing Sheets

(56) References Cited

OTHER PUBLICATIONS

Goh, B.C., et al., "Cryopreservation characteristics of adipose-derived stem cells: maintenance of differentiation potential and viability," J Tissue Eng Regen Med 1:322-324 (2007).

Ma, W., et al., "Cryopreservation of adherent neuronal networks," Neuroscience Letters 403:84-89 (2006).

Kilroy, G.E., et al., "Cytokine Profile of Human Expression of Angiogenic,Hematopoietic, and Pro-Inflammatory Factors," J. Cell. Physiol. 212: 702-709 (2007).

Wilson, A., et al., "Adipose-derived stem cells for clinical applications: a review," Cell Prolif. 44: 86-98 (2011).

Lee, E.J., et al., "Human Embryonic Stem Cells: Derivation, Maintenance and Cryopreservation," International Journal of Stem Cells 4:9 (2011).

Black, et al. "Effect of Adipose-Derived Mesenchymal Stem and Regenerative Cells on Lameness in Dogs with Chronic Osteoarthritis of the Coxofemoral Joints: A Randomized, Double-Blinded, Multicenter, Controlled Trial," Veterinary Therapeutics, vol. 8(4): 272-284 (2007).†

\* cited by examiner
† cited by third party

THERAPEUTICS USING ADIPOSE CELLS AND CELL SECRETIONS

RELATED APPLICATIONS

The present application is a US national phase of International Application No. PCT/AU2012/001140 filed on Sep. 21, 2012, which claims benefit from Australian provisional patent application No. 2011903938 entitled "Therapeutic methods and compositions" filed on 23 Sep. 2011 and from Australian provisional patent application No. 2012901350 entitled "Therapeutic methods and compositions" filed on 4 Apr. 2012 and from Australian provisional patent application No. 2012903646 entitled "Therapeutic methods and compositions" filed on 23 Aug. 2012, the entire contents of each of which is incorporated herein by reference.

TECHNICAL FIELD

The present invention relates to compositions comprising (i) adipose tissue-derived cell secretions or (ii) an adipose tissue-derived cell suspension, optionally comprising adipocytes or (iii) a combination of adipose tissue-derived cell secretions and an adipose tissue-derived cell suspension, optionally comprising adipocytes, and to their use in pharmaceutical compositions and methods for treatment of various conditions such as inflammatory disorders, ligament injuries, tendon injuries, or for alleviating pain associated with such conditions, an inflammatory disorder, a ligament injury or a tendon injury, in a mammalian subject. In the methods of the invention the compositions are administered to a site on a patient remote to the site affected by the inflammatory disorder or condition. The invention also relates to the use of such compositions in pharmaceutical compositions and methods for the treatment or prevention of disease in an intensively farmed animal, wherein said administration is by subcutaneous or intramuscular injection. The invention also relates to the treatment of pain in a subject, the treatment being by subcutaneous injection or intramuscular injection. The invention also relates to treatment of neuropathic pain in a subject. The invention also relates to improved methods, agents and compositions for cryopreservation of cells.

BACKGROUND OF THE INVENTION

Adipose tissue contains a cell population of large lipid filled adipocytes, and a non-adipocyte cell population, which comprises cells associated with various connective fibres and cells associated with capillaries and larger blood vessels. The non-adipocyte cell population is also thought to comprise a population of adipose-derived adult stem cells and consequently there has been interest in using adipose tissue as a source of isolated stem cells for various therapeutic applications.

In general, methods for obtaining adipose tissue derived presumptive stem cells involves depleting adipocytes from adipose-derived non-adipocyte cells, which requires digesting adipose tissue with enzymes such as collagenase, and then separating the liberated cells by centrifuging the digested sample. During centrifugation, the adipose-derived non-adipocyte cells separate from the adipocytes to form a pellet, whereas the lipid containing adipocytes float. The non-adipocyte cell fraction is then used as a source of tissue stem cells.

The present inventors have earlier described the use of an adipose tissue-derived cell suspension which comprises adipocytes for the preparation of a pharmaceutical composition for use in the treatment of an inflammatory disorder or the alleviation of pain associated with an inflammatory disorder in a subject, and for the treatment and alleviation of pain of conditions such as a cartilage or bone disorders. This is described in Australian Patent Application No. 2009201915 and in International Publication No. WO2010/020005, the contents of which are incorporated herein by cross-reference. The present inventors have also earlier described the use of adipose tissue-derived cells secretions for the preparation of compositions for use in treatment of various conditions and diseases, including in the alleviation of pain associated with such conditions.

Generations of selective breeding of animals for certain desirable traits, such as rapid growth, efficient feed conversion and muscle mass accumulation in animals raised for meat production, or milk quality and volume in dairy animals, has also resulted in modern breeds of animals often being prone to a higher incidence of detrimental health conditions than less intensively bred or selected animals, such as wild populations. The clinical incidence or effect of such detrimental traits can be exacerbated by the manner in which the animals are farmed, such as in intensive farming operations. Modern pig breeds, farmed under intensive conditions for example, are prone to leg weakness, such as osteochondrosis (OCD), arthritis, a high risk of clinical and sub-clinical bacterial infection, all of which have the potential to detrimentally affect the general well-being of the animal and hence detrimentally affect the farming operation.

There remains a need for improved methods for the treatment of inflammatory conditions, ligament and tendon injuries and compositions for use therein. There remains a need for improved methods for the treatment and prevention of detrimental conditions associated with intensive animal farming. There remains a need for the treatment of pain in a subject and compositions for use therein.

SUMMARY OF THE INVENTION

Methods previously described for the treatment of inflammatory disorders using adipose tissue-derived cell suspensions and cell free compositions teach the administration of the composition or suspension to the afflicted area, such as by intra-articular injection in the case of an arthritic joint. Surprisingly, the inventor has now identified that direct administration of the therapeutic composition to the afflicted area is not required. The inventor has surprisingly identified that the remote delivery of a composition comprising secretions from an adipose tissue-derived cell suspension or of a composition comprising an adipose tissue-derived cell suspension, optionally comprising adipocytes, or of a combination thereof, can also be effective in the treatment of such conditions.

The inventors have surprisingly identified that frozen stem cells, such as mesenchymal stem cells, such as adipose tissue-derived stem cells, may be used as therapeutic agents in treatment of various conditions. Surprisingly such frozen cells may be used without the need for culturing the cells after retrieval from frozen storage. The inventors have also identified that storage of cells in the presence of cell-derived secretions improves the viability and proliferation potential of cryopreserved stem cells, including cells derived from adipose tissue.

Accordingly, in a first aspect of the invention there is provided a method of treating a condition selected from the group consisting of an inflammatory disorder, a ligament injury and a tendon injury, or alleviating pain associated with an inflammatory disorder, a ligament injury or a tendon injury, in a subject, comprising administering to the subject a pharmaceutical composition which comprises (i) adipose tissue-derived cell secretions, or (ii) an adipose tissue-derived cell suspension, optionally comprising adipocytes or (iii) a combination of (i) and (ii), wherein said administration to said subject is at a site remote from the site of said condition. In an embodiment the subject is a mammalian subject. In an embodiment the adipose tissue-derived cell suspension, optionally comprising adipocytes comprises aggregates of cells and or comprises pieces of adipose tissue. In an embodiment the cell suspension comprises adipocytes. In an embodiment the cell suspension is substantially free of adipocytes. In an embodiment the adipose tissue-derived cell secretions comprises a carrier liquid selected from cell culture media and distilled water. In an embodiment an adipose tissue-derived cell suspension, optionally comprising adipocytes, or a combination of an adipose tissue-derived cell secretions and an adipose tissue-derived cell suspension, optionally comprising adipocytes comprises a carrier liquid being a cell culture medium, such as DMEM.

In an embodiment the inflammatory disorder or condition is selected from the group consisting of osteoarthritis, stifle disease, wobblers, a tendon injury and a ligament injury. In an embodiment the inflammatory disorder is atopic dermatitis. In an embodiment the inflammatory disorder or condition is selected from the group consisting of rheumatoid arthritis, back pain, and multiple sclerosis. In an embodiment the inflammatory disorder or condition is an immune driven disease. In an embodiment the method comprises administration of adipose tissue-derived cell secretions. In an embodiment the method comprises administration of an adipose tissue-derived cell suspension. In an embodiment the administration is subcutaneous administration. In an embodiment the administration is intra-muscular administration. In an embodiment the administration is in the rump, arm, or buttocks. In an embodiment the administration is into the neck of the subject, such as the nape of the subject, such as the scruff of the neck when the subject is a dog or cat.

In a second aspect there is provided a method of treating a joint disease or condition in a subject, the method comprising administering to the subject a pharmaceutical composition which comprises (i) adipose tissue-derived cell secretions, or (ii) an adipose tissue-derived cell suspension, optionally comprising adipocytes, or (iii) a combination of (i) and (ii), wherein said administration to said subject is at a site remote from the site of said condition. In an embodiment the subject is a mammalian subject. In an embodiment the adipose tissue-derived cell suspension, optionally comprising adipocytes, comprises aggregates of cells and or comprises pieces of adipose tissue. In an embodiment the adipose tissue-derived cell secretions comprises a carrier liquid selected from cell culture media and distilled water. In an embodiment an adipose tissue-derived cell suspension, optionally comprising adipocytes, or a combination of an adipose tissue-derived cell secretions and an adipose tissue-derived cell suspension, optionally comprising adipocytes, comprises a carrier liquid being a cell culture medium, such as DMEM. In an embodiment the treatment comprises administering a pharmaceutical composition comprising an adipose tissue-derived cell suspension to said mammal by subcutaneous injection. In an embodiment the subcutaneously administered cell suspension is substantially free of adipocytes. In an embodiment the subcutaneously administered cell suspension comprises adipocytes.

In an embodiment the mammalian subject is an equine, feline, canine, bovine or porcine animal. In an embodiment the subject is a human. In an embodiment the subject is poultry.

In an embodiment the administration is subcutaneous administration. In an embodiment the administration is intra-muscular administration. In an embodiment the administration is in the rump, arm, or buttocks. In an embodiment the administration is into the neck of the subject, such as the nape of the subject, such as the scruff of the neck when the subject is a dog or cat.

In a third aspect of the invention there is provided a method for the treatment or prevention of a disease in an intensively farmed animal, the method comprising administering to the animal a pharmaceutical composition which comprises (i) adipose tissue-derived cell secretions, or (ii) an adipose tissue-derived cell suspension, optionally comprising adipocytes, or (iii) a combination of adipose tissue-derived cell secretions and an adipose tissue-derived cell suspension, optionally comprising adipocytes, wherein said administration is by subcutaneous injection or intramuscular injection.

In an embodiment the disease of an intensively farmed animal is an orthopeadic developmental disease. In an embodiment the disease of an intensively farmed animal is selected from the group consisting of leg weakness, lameness, arthritis, developmental diseases and bacterial infection. In an embodiment the developmental disease is osteochondrosis (OCD).

In an embodiment the pharmaceutical composition is administered to an animal prior to the onset of clinical symptoms of the disease. In an embodiment the intensively fanned animal is a pig and the pharmaceutical composition is administered prior to the onset of clinical symptoms of the orthopeadic developmental disease, such as osteochondrosis.

In an embodiment the intensively farmed animal is selected from the group consisting of pigs, cattle, sheep, and poultry, In an embodiment the intensively farmed animal is a breeder female. In an embodiment the intensively farmed animal is a pregnant female. In an embodiment the animal is a pregnant sow. In an embodiment the pregnant sow has clinical symptoms of osteochondrosis or arthritis.

In an embodiment the administration is subcutaneous administration. In an embodiment the administration is intra-muscular administration. In an embodiment the administration is into the neck of the subject, such as the nape of the subject.

The following embodiments apply to all aspects of the invention herein, unless the context clearly indicates otherwise.

In an embodiment the adipose tissue-derived cell secretions are prepared from an adipose tissue-derived cell suspension. In an embodiment the adipose tissue-derived cell suspension is substantially free of adipocytes. In an embodiment the adipose tissue-derived cell suspension further comprises adipocytes. In an embodiment the adipose tissue-derived cell suspension comprises mature adipocytes. In an embodiment the adipose tissue-derived cell secretions are prepared by culture of adipose tissue-derived cell suspension. In an embodiment the adipose tissue-derived cell suspension is substantially free of adipocytes. In an embodiment the adipose tissue-derived cell suspension further comprises adipocytes. In an embodiment the adipose tissue-derived cell suspension, optionally comprising adipocytes comprises aggregates of cells and or comprises pieces of adipose tissue.

In an embodiment the adipose tissue-derived cell suspension is prepared by a method that comprises removal of (i) part of the adipocyte content or (ii) substantially all of the adipocyte content during preparation of the adipose tissue-derived cell suspension.

In an embodiment the adipose tissue-derived cell secretions is a concentrated preparation. In an embodiment the concentrated preparation is concentrated in comparison to the cell secretions as initially harvested from the adipose tissue-derived cell suspensions or culture thereof. In an embodiment the adipose tissue-derived cell secretions is a preparation concentrated by between about 2-fold and about 20-fold. In an embodiment the adipose tissue-derived cell secretions is a preparation concentrated by about 10-fold.

In an embodiment the adipose tissue-derived cell secretions is of bovine, canine, porcine or equine origin. In an embodiment the adipose tissue-derived cell secretions is of human origin.

In an embodiment, the adipose tissue-derived cell secretions is derived from adipose tissue autologous to the recipient subject or animal. In an embodiment the adipose tissue-derived cell secretions is derived from adipose tissue allogeneic to the recipient subject or animal. In an embodiment the adipose tissue-derived cell secretions is derived from adipose tissue xenogeneic to the recipient subject or animal.

In an embodiment the adipose tissue-derived cell suspension, optionally comprising adipocytes, comprises mature adipocytes.

In an embodiment the adipose tissue-derived cell suspension, optionally comprising adipocytes is of bovine, canine, porcine or equine origin. In an embodiment the adipose tissue-derived cell suspension, optionally comprising adipocytes is derived from adipose tissue autologous to the recipient subject or animal. In an embodiment the adipose tissue-derived cell suspension, optionally comprising adipocytes is derived from adipose tissue allogeneic to the recipient subject or animal. In an embodiment the adipose tissue-derived cell suspension, optionally comprising adipocytes is derived from adipose tissue xenogeneic to the recipient subject or animal.

In an embodiment the adipose tissue-derived cell suspension, optionally comprising adipocytes is a cell suspension obtained by cell expansion in culture.

In an embodiment the adipose tissue-derived cell secretions, or a pharmaceutical composition thereof are stored frozen prior to administration.

In an embodiment the adipose tissue-derived cell suspension, optionally comprising adipocytes, or a pharmaceutical composition thereof are stored frozen prior to administration.

In an embodiment the adipose tissue-derived cell secretions in combination with adipose tissue-derived cell suspension, optionally comprising adipocytes, or a pharmaceutical composition thereof is stored frozen prior to administration. In an embodiment the cell secretions in said combination are a concentrated preparation. In an embodiment the preparation is concentrated by between 2-fold and 20-fold in comparison to the secretions prior to concentration.

In an embodiment the method further comprises (i) thawing frozen adipose tissue-derived cell secretions, or (ii) thawing frozen adipose tissue-derived cell suspension, optionally comprising adipocytes, or (iii) thawing a frozen combination of adipose tissue-derived cell secretions and an adipose tissue-derived cell suspension, optionally comprising adipocytes, or (iv) thawing a frozen pharmaceutical composition of any of (i), (ii) or (iii), prior to administration to the recipient subject or animal.

In an embodiment the frozen secretions, cell suspension, combination thereof, or pharmaceutical composition thereof, is administered to the recipient subject or animal soon after thawing, such as within about 10 minutes after thawing, or within about 20 minutes after thawing, or within about 30 minutes after thawing or within about one hour of thawing or within about two hours of thawing.

In an embodiment the method further comprises combining (i) a composition comprising adipose tissue-derived cell secretions and (ii) an adipose tissue-derived cell suspension, optionally comprising adipocytes, prior to administering said combination to the recipient subject or animal. In an embodiment said combining occurs within 2 hours before said administration. In an embodiment one or both of said composition comprising adipose tissue-derived cell secretions and said adipose tissue-derived cell suspension, optionally comprising adipocytes, is stored frozen prior to said combining. In a further embodiment the composition comprising adipose tissue-derived cell secretions and said adipose tissue-derived cell suspension, optionally comprising adipocytes, are mixed together before the composition is frozen.

In an embodiment the pharmaceutical composition is a veterinary composition and the subject is a non-human animal.

In a fourth aspect of the invention there is provided use of (i) adipose tissue-derived cell secretions, or (ii) an adipose tissue-derived cell suspension, optionally comprising adipocytes, or (iii) a combination of (i) and (ii), for the preparation of a pharmaceutical composition for use in the treatment of a condition selected from the group consisting of an inflammatory disorder, a ligament injury and a tendon injury, or alleviating pain associated with an inflammatory disorder, a ligament injury or a tendon injury, in a mammalian subject, wherein the composition is suitable for administration to a site of said subject remote from the site of said condition.

In a fifth aspect there is provided use of (i) adipose tissue-derived cell secretions, or (ii) an adipose tissue-derived cell suspension, optionally comprising adipocytes, or (iii) a combination of (i) and (ii), for the preparation of a pharmaceutical composition for use in the treatment of a joint disease or condition in a mammalian subject, wherein the composition is suitable for administration to a site of said subject remote from the site of said condition. In an embodiment the adipose tissue-derived cell suspension, optionally comprising adipocytes, comprises aggregates of cells and or comprises pieces of adipose tissue. In an embodiment the adipose tissue-derived cell suspension is substantially free of adipocytes. In an embodiment the adipose tissue-derived cell suspension comprises adipocytes.

In a sixth aspect of the invention there is provided use of (i) adipose tissue-derived cell secretions, or (ii) an adipose tissue-derived cell suspension, optionally comprising adipocytes, or (iii) a combination of (i) and (ii), for the preparation of a pharmaceutical composition for use in the treatment or prevention of disease in an intensively farmed animal, wherein the composition is suitable for subcutaneous injection or intramuscular injection.

In a seventh aspect of the invention there is provided a composition comprising (i) adipose tissue-derived cell secretions, or (ii) an adipose tissue-derived cell suspension, optionally comprising adipocytes, or (iii) a combination of (i) and (ii), for treatment of a condition selected from the group consisting of an inflammatory disorder, a ligament injury and a tendon injury, or alleviating pain associated with an inflammatory disorder, a ligament injury or a tendon injury, wherein the composition is administered to a site on a subject remote from the site afflicted by the condition. In an embodiment the composition is an injectable composition. In an embodiment the administration is by subcutaneous injection or intramuscular injection.

In an eighth aspect of the invention there is provided a composition comprising (i) adipose tissue-derived cell secretions, or (ii) an adipose tissue-derived cell suspension, optionally comprising adipocytes, or (iii) a combination of (i) and (ii), for treatment of a joint disease or condition in a mammalian subject, wherein said composition is administered a site of said subject remote from the site of said condition. In an embodiment the adipose tissue-derived cell suspension, optionally comprising adipocytes, comprises aggregates of cells and or comprises pieces of adipose tissue. In an embodiment the adipose tissue-derived cell suspension is substantially free of adipocytes. In an embodiment the adipose tissue-derived cell suspension comprises adipocytes.

In a ninth aspect of the invention there is provided a composition comprising (i) adipose tissue-derived cell secretions, or (ii) an adipose tissue-derived cell suspension, optionally comprising adipocytes, or (iii) a combination of (i) and (ii), for treatment or prevention of a disease in an intensively farmed animal, wherein in said treatment or prevention the composition is administered by subcutaneous injection or intramuscular injection.

In a tenth aspect of the invention there is provided a pharmaceutical composition comprising (i) adipose tissue-derived cell secretions, or (ii) an adipose tissue-derived cell suspension, optionally comprising adipocytes, or (iii) a combination of (i) and (ii), together with a pharmaceutically acceptable carrier, diluent, excipient or adjuvant. In an embodiment the composition comprising adipose tissue-derived cell secretions further comprises adipocytes. In an embodiment the composition is a frozen composition.

In an eleventh aspect of the invention there is provided a kit comprising (a) a pharmaceutical composition selected from the group consisting of (i) a composition comprising adipose tissue-derived secretions, (ii) a composition comprising an adipose tissue-derived cell suspension, optionally comprising adipocytes, and (iii) a combination of (i) and (ii); and (b) instructions for use of said kit in treatment of a condition selected from the group consisting of an inflammatory disorder, a ligament injury and a tendon injury, or alleviating pain associated with an inflammatory disorder, a ligament injury or a tendon injury; wherein said treatment comprises administration of said pharmaceutical composition to a site on a subject remote from the site afflicted by the condition.

In a twelfth aspect of the invention there is provided a kit comprising (a) a pharmaceutical composition selected from the group consisting of (i) a composition comprising adipose tissue-derived secretions, (ii) a composition comprising an adipose tissue-derived cell suspension, optionally comprising adipocytes, and (iii) a combination of (i) and (ii); and (b) instructions for use of said kit in treatment of a joint disease or condition in a mammalian subject, wherein said treatment comprises administration of said pharmaceutical composition to a site on a subject remote from the joint afflicted by the joint disease or condition. In an embodiment the adipose tissue-derived cell suspension, optionally comprising adipocytes, comprises aggregates of cells and or comprises pieces of adipose tissue. In an embodiment the adipose tissue-derived cell suspension is substantially free of adipocytes. In an embodiment the adipose tissue-derived cell suspension comprises adipocytes.

In a thirteenth aspect of the invention there is provided a kit comprising (a) a pharmaceutical composition selected from the group consisting of (i) a composition comprising adipose tissue-derived secretions, (ii) a composition comprising an adipose tissue-derived cell suspension, optionally comprising adipocytes, and (iii) a combination of (i) and (ii); and (b) instructions for use of said kit in treatment or prevention of disease in an intensively farmed animal, wherein in said treatment or prevention the composition is administered by subcutaneous injection or intramuscular injection.

In an embodiment the kit comprises one or more frozen compositions. In an embodiment the kit comprises instructions for combining a composition comprising adipose tissue-derived secretions and a composition comprising an adipose tissue-derived cell suspension, optionally comprising adipocytes, prior to administration of a combined composition. In an embodiment the kit further comprises one or more injection devices, such as one or more syringes. In an embodiment the injection device contains a composition of the kit.

In a fourteenth aspect of the invention there is provided a method of alleviating pain in a mammalian subject, the method comprising administering to the subject a pharmaceutical composition which comprises (i) adipose tissue-derived cell secretions, or (ii) an adipose tissue-derived cell suspension, optionally comprising adipocytes, or (iii) a combination of (i) and (ii), wherein said administration to said subject is by intramuscular injection or by subcutaneous injection or by an appropriate form of administration at or near a site of the pain. In an embodiment the pain is associated with a condition selected from the group consisting of an inflammatory disorder, a ligament injury and a tendon injury. In an embodiment the pain is associated with osteoarthritis, stifle disease, wobblers, a tendon injury or a ligament injury. In an embodiment the pain is associated with atopic dermatitis. In an embodiment the pain is associated with rheumatoid arthritis, back pain, or multiple sclerosis. In an embodiment the pain is associated with a condition selected from the group consisting of leg weakness, lameness, arthritis, developmental diseases and bacterial infection. In an embodiment the pain is associated with osteochondrosis (OCD). In an embodiment the pain is associated with a burn injury. In an embodiment the pain is neck and or shoulder pain, whiplash associated disorder, or complex regional pain syndrome. In an embodiment the pain is back pain. In an embodiment the pain is lower back pain. In an embodiment the pain is pain associated with a sciatic disorder. In an embodiment the treatment is of pain for which there is no discernable causative clinical condition. In an embodiment the treatment is of pain for which there is no discernable causative clinical condition in the part or region of the body in which the subject experiences the pain. In an embodiment the pain is neuropathic pain. In an embodiment the neuropathic pain is pain for which there is no discernable causative clinical condition. In an embodiment the appropriate form of administration is injection. In an embodiment the appropriate form of administration is topical application. The neuropathic pain may be localised to one area of the body or it may be experienced in multiple sites of the subject's body. When experienced in multiple sites, the intensity of the pain may be similar at multiple sites or it may be different at multiple sites. In an embodiment the neuropathic pain is neuropathic facial pain. In an embodiment the pain is neuropathic facial pain and administration to said subject is by injection into the jaw or the gum. In an embodiment the injection into the jaw or the gum is at the original site of the pain. In an embodiment the pain is associated with a joint disease or joint disorder and the composition is administered to a site on said subject which is remote to said joint. In an embodiment the adipose tissue-derived cell suspension, optionally comprising adipocytes, comprises aggregates of cells and or comprises pieces of adipose tissue.

In a fifteenth aspect of the invention there is provided use of (i) adipose tissue-derived cell secretions, or (ii) an adipose tissue-derived cell suspension, optionally comprising adipocytes, or (iii) a combination of (i) and (ii), for the preparation of a pharmaceutical composition for use in alleviating pain in a mammalian subject, wherein the pharmaceutical composition is suitable for administration to said subject by intramuscular injection or by subcutaneous injection or by an appropriate form of administration, such as topical administration, at or near a site of the pain.

In a sixteenth aspect of the invention there is provided a composition comprising (i) adipose tissue-derived cell secretions, or (ii) an adipose tissue-derived cell suspension, optionally comprising adipocytes, or (iii) a combination of (i) and (ii), for alleviating pain in a mammalian subject, wherein the pharmaceutical composition is administered to said subject by intramuscular injection or by subcutaneous injection or by an appropriate form of administration, such as topical administration, at or near a site of the pain.

In a seventeenth aspect of the invention there is provided a kit comprising (a) a pharmaceutical composition selected from the group consisting of (i) a composition comprising adipose tissue-derived secretions, (ii) a composition comprising an adipose tissue-derived cell suspension, optionally comprising adipocytes, and (iii) a combination of (i) and (ii); and (b) instructions for use of said kit in alleviating pain in a mammalian subject, wherein the pharmaceutical composition is administered to said subject by intramuscular injection or by subcutaneous injection or by an appropriate form of administration, such as topical administration, at or near a site of the pain.

In a further aspect the invention provides a composition comprising adipose tissue-derived cells and adipose tissue-derived cell secretions. In an embodiment the cells are adherent cells. In an embodiment the cells are mesenchymal stem cells. In an embodiment the composition is a frozen composition. In an embodiment the adipose tissue-derived cell secretions comprise clarified media from culture of adipose tissue-derived cells. In an embodiment the adipose tissue-derived cell secretions is a concentrated preparation of media from culture of adipose tissue-derived cells. In an embodiment the adipose tissue-derived cell secretions is a preparation concentrated between 2-fold and 20-fold. In an embodiment the composition further comprises adipocytes. In an embodiment the cells are progeny cells from culture of an adipose tissue-derived cell suspension. In an embodiment the cells comprise a cell line obtained by culture of an adipose tissue-derived cell suspension. In an embodiment the progeny cells are from multiple passaging of cells derived from an adipose tissue-derived cell suspension. In an embodiment the multiple passaging comprises five or more passages. In an embodiment the multiple passaging comprises ten or more passages. In an embodiment the composition comprises cells of an adipose tissue-derived cell line which has been frozen multiple times.

In a further aspect the invention provides a method for the cryopreservation of a stored cell, the method comprising combining said cell with a composition comprising cell secretions and storing said combination in a frozen state. In an embodiment the method is for the cryopreservation of a cell line. In an embodiment, prior to said storing, the combination is held at room temperature for up to one hour. In an embodiment the said stored cell is an adherent cell. In an embodiment the stored cell is a mesenchymal stem cell. In an embodiment the stored cell is an adipose tissue-derived cell. In an embodiment the cell line is an adipose tissue-derived cell line. In an embodiment the composition comprising cell secretions comprises clarified media from culture of an adipose tissue-derived cell suspension. In an embodiment the culture of an adipose tissue-derived cell suspension is culture of progeny cells of an adipose tissue-derived cell suspension. In an embodiment the composition comprising cell secretions comprises concentrated media from culture of an adipose tissue-derived cell suspension. In an embodiment the composition comprising cell secretions comprises media from culture of an adipose tissue-derived cell suspension concentrated between 2-fold and 20-fold. In an embodiment the cell line has been passaged multiple times. In an embodiment the cell line has been passaged more than five times. In an embodiment the cell line has been passaged more than ten times. In an embodiment the cell line has been passaged more than fifteen times. In an embodiment the cell line has been frozen multiple times.

It will be understood that embodiments described herein apply equally to any and all aspects of the invention described herein, they are simply not repeated under each aspect of the invention for the sake of brevity.

The summary of the invention described above is not limiting and other features and advantages of the invention will be apparent from the following detailed description of the preferred embodiments, as well as from the claims.

ABBREVIATIONS

Figure 1:
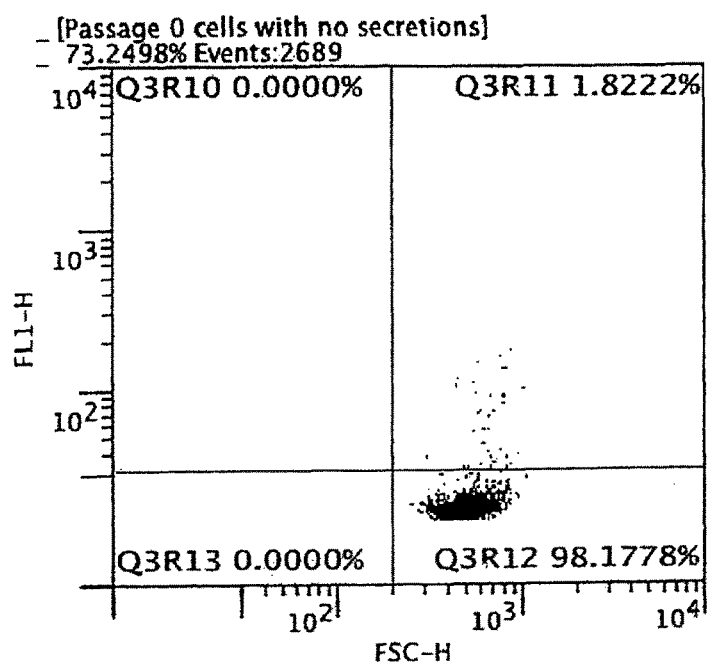
FIG. 1: Proliferation of cells after freezing. Cells that had not been passaged and were frozen without secretions (left graph) and with secretions (right graph) were stained with the Click-iT ERD assay that identifies proliferating cells. The proliferating cells appear in the upper right quadrant.
Figure 1:
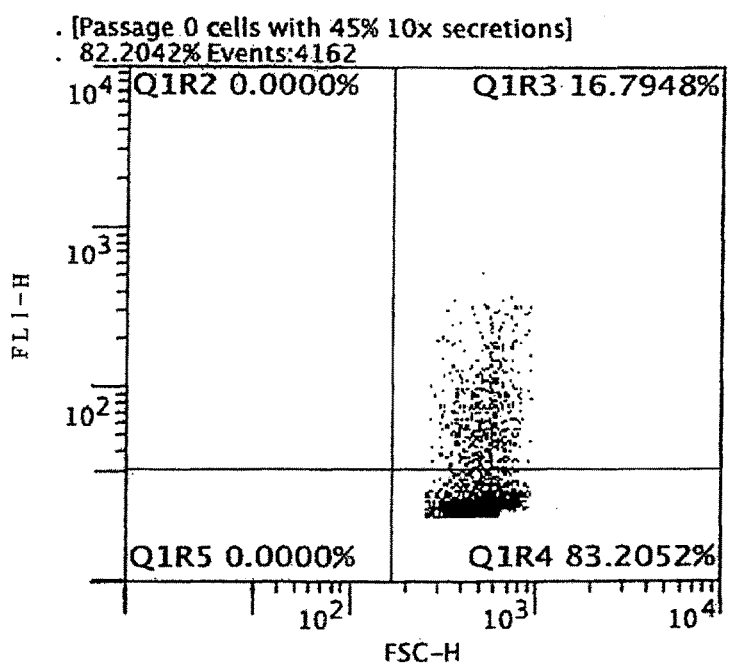

DMEM Dulbecco's Modified Eagles Medium.
SVCs stromal vascular cells.
SVF stromal vascular fraction.
OCD osteochondrosis.
MSC mesenchymal stem cell(s).

Definitions

In the context of the present invention reference to a composition comprising "adipose tissue-derived secretions" will be understood to mean a composition which includes one or more factors released from cells of the adipose tissue. The material used in the preparation of the composition comprising the secretions may or may not include adipocytes.

The term "pharmaceutically acceptable" as used herein in the context of various components relevant to the invention, such as carriers, diluents, cryopreservatives, is intended to encompass not only such components which are suitable for administration to a human subject, but also those suitable for administration to a non-human mammalian subject. In particular embodiments, the pharmaceutically acceptable component is suitable for administration to a non-human mammalian subject. In particular embodiments the pharmaceutically acceptable component is suitable for administration to a human subject. In particular embodiments, the pharmaceutically acceptable component is suitable for administration to a non-human mammalian subject and to a human subject.

The terms "treating", "treatment", "therapy" and the like in the context of the present specification refer to the alleviation of the symptoms and/or the underlying cause of the condition or disease, such as inflammatory disorder, ligament injury, or tendon injury or disease of an intensively farmed animal. In certain embodiments a treatment will slow, delay or halt the progression of a disorder or the symptoms of the disorder or injury, or reverse the progression of the disorder or injury, at least temporarily. Hence, in the context of this invention the word "treatment" or derivations thereof such as "treating" when used in relation to a therapeutic application includes all aspects of a therapy, such as the alleviation of pain associated with the condition being treated, alleviation of the severity of the condition being treated, improvement in one or more symptoms of the condition being treated, etc. Use of the word "treatment" or derivatives thereof will be understood to mean that the subject being "treated" may experience any one or more of the aforementioned benefits.

The term "preventing" and the like, in the context of the "prevention" of disease, refers to hindrance of the progression of the symptoms or the underlying cause of the disease. It will be understood that complete prevention of a disease may occur, such that the disease does not occur in a treated animal or subject. Equally, it will be understood that the term includes partial prevention, such as the failure of a disease to progress to the typical state observed in an animal or subject left untreated.

Throughout this specification, reference to "a" or "one" element does not exclude the plural, unless context determines otherwise. Similarly, reference to "an embodiment" does not exclude the characteristic of that described embodiment applying in combination with one or more other embodiments described, unless the context determines otherwise.

The term "therapeutically effective amount" as used herein includes within its meaning a non-toxic but sufficient amount of a compound or composition for use in the invention to provide the desired therapeutic effect. The exact amount required will vary from subject to subject depending on factors such as the species being treated, the age and general condition of the subject, co-morbidities, the severity of the condition being treated, the particular agent being administered and the mode of administration and so forth. Thus, for any given case, an appropriate "effective amount" may be determined by one of ordinary skill in the art using only routine methods.

In the context of this specification, the term "comprising" means including, but not necessarily solely including. Furthermore, variations of the word "comprising", such as "comprise" and "comprises", have correspondingly varied meanings. Hence, the term "comprising" and variations thereof is used in an inclusive rather than exclusive meaning such that additional integers or features may optionally be present in a composition, method, etc. that is described as comprising integer A, or comprising integer A and B, etc.

In the context of this specification the term "about" will be understood as indicating the usual tolerances that a skilled addressee would associate with the given value.

In the context of this specification, where a range is stated for a parameter it will be understood that the parameter includes all values within the stated range, inclusive of the stated endpoints of the range. For example, a range of "5 to 10" will be understood to include the values 5, 6, 7, 8, 9, and 10 as well as any sub-range within the stated range, such as to include the sub-range of 6 to 10, 7 to 10, 6 to 9, 7 to 9, etc, and inclusive of any value and range between the integers which is reasonable in the context of the range stated, such as 5.5, 6.5, 7.5, 5.5 to 8.5 and 6.5 to 9, etc.

In the context of this specification, the term "plurality" means any number greater than one.

It is to be noted that reference herein to use of the inventive methods and compositions in treatment or therapy will be understood to be applicable to human and non-human, such as veterinary, applications. Hence it will be understood that, except where otherwise indicated, reference to a patient, subject or individual means a human or a non-human, such as an individual of any species of social, economic, agricultural or research importance including but not limited to members of the classifications of ovine, bovine, equine, porcine, feline, canine, primates, rodents, especially domesticated or farmed members of those classifications, such as sheep, cattle, horses, pigs and dogs.

Where examples of various embodiments or aspects of the invention are described herein they will generally be prefaced by appropriate terms including "such as" or "for example", or "including". It will be understood that the examples are being described as inclusive possibilities, such as for the purpose of illustration or understanding and are not, unless the context indicates otherwise, being provided as limiting.

The pharmaceutical composition referred to herein may also be referred to as a medicament when intended for therapeutic use. Hence, it will be understood that where the invention is described as including the use of a composition of described components for the preparation of a pharmaceutical composition for an intended therapeutic purpose, that description equally means use for the preparation of a medicament for that intended therapeutic purpose, unless the context indicates otherwise.

To the extent that it is permitted, all references cited herein are incorporated by reference in their entirety.

DETAILED DESCRIPTION OF THE PREFERRED EMBODIMENTS

The present inventors have identified that surprisingly the remote delivery of a composition comprising secretions from an adipose tissue-derived cell suspension can be effective in the treatment of various conditions including inflammatory diseases and bone and joint disorders, including ligament injuries and tendon injuries. The inventors have also surprisingly identified that remote delivery of an adipose tissue-derived cell suspension, optionally comprising adipocytes, or of a combination of adipose tissue-derived secretions and an adipose tissue-derived cell suspension, optionally comprising adipocytes, can be effective in the treatment of such conditions. Previously described methods for the treatment of such conditions have described the administration of the therapeutic to a site of disease or pain by direct application, such as intra-articular injection in the case of a joint disease. The present invention thus pertains to methods of treating such conditions by remote administration of (i) a composition comprising adipose tissue-derived cell secretions, or (ii) a composition comprising an adipose tissue-derived cell suspension, optionally comprising adipocytes, or (iii) a combination of (i) and (ii), to a subject in need thereof. The invention also provides for the use of (i) adipose tissue-derived cell secretions, or (ii) an adipose tissue-derived cell suspension, optionally comprising adipocytes, or (iii) a combination of (i) and (ii), for the preparation of a medicament for the treatment of a condition selected from the group consisting of an inflammatory disorder, a ligament injury and a tendon injury, or alleviating pain associated with an inflammatory disorder, a ligament injury, a tendon injury, neuropathic pain, or a burn injury, the medicament suitable for remote administration to a subject.

As described herein, the inventor has surprisingly identified that administration of such a therapeutic agent does not necessarily need to be direct administration of the agent to the diseased or affected site, such as a joint. By administration of the therapeutic agent, such as by subcutaneous injection or intramuscular injection, the inventor has identified that various diseases may be treated or prevented. In the case of a disease affecting a joint, the description herein of the administration as remote simply means that it is not administered directly into the joint, but rather is typically administered by subcutaneous injection or intramuscular injection. Hence, the site of administration by subcutaneous injection or intramuscular injection may or may not be particularly distant from the affected joint. The invention pertains also to methods for the treatment or prevention of disease in an intensively farmed animal, the method comprising administration by subcutaneous injection or intramuscular injection of (i) a composition comprising adipose tissue-derived cell secretions, or (ii) an adipose tissue-derived cell suspension, optionally comprising adipocytes, or (iii) a combination of (i) and (ii).

The inventor has identified that allogeneic and xenogeneic compositions can be used in the treatment and further that the therapeutic compositions can be stored frozen prior to use. It will be understood that in an aspect the invention herein relates to such compositions per se, regardless of the manner in which they may be used or may be intended to be used. In other aspects, the invention relates to the use of compositions of the invention in the methods disclosed herein. In this manner so-called "off the shelf" or "ready to use" therapeutic products offering advantages, such as of supply, ease of use, less patient discomfort, and a lower requirement for technical skills, compared to an autologous patient-derived therapeutic agent, can be made available. The present invention thus permits the preparation of the therapeutic agent in advance of patient contact, such that a product comprising adipose tissue-derived cell secretions or an adipose tissue-derived cell suspension, optionally comprising adipocytes, may be made available without the need to anesthetize a subject or animal for extraction of adipose tissue. Similarly, where the therapeutic agent is a combination of adipose tissue-derived cell secretions and an adipose tissue-derived cell suspension, optionally comprising adipocytes, that combination may be made available to the user, such as a clinician, veterinarian, or farmer in advance or the separate compositions of cell secretions and of cell suspension may be supplied, with the user then preparing the combination shortly before administration. As described herein the cell secretions, the cell suspension, or the combination can be stored, for example at $-20°$ C. until required for use. Alternatively, the cell secretions, the cell suspension, or the combination may be stored at a lower temperature, such as in a freezer at $-70°$ C. to $-90°$ C., or in liquid nitrogen storage, either in the vapour phase or in the liquid phase, until required for use. Compositions comprising cells will typically be stored in liquid nitrogen. In a preferred embodiment the composition comprising adipose tissue-derived cell secretions, or the adipose tissue-derived cell suspension, optionally comprising adipocytes; or the combination of adipose tissue-derived cell secretions and adipose tissue-derived cell suspension, optionally comprising adipocytes, is stored in the liquid phase of liquid nitrogen storage. In an embodiment the adipose tissue-derived cell secretions is a concentrated preparation. In an embodiment the concentrated preparation is concentrated in comparison to the cell secretions as initially harvested from the adipose tissue-derived cell suspensions or culture thereof. In an embodiment the adipose tissue-derived cell secretions is a preparation concentrated by between about 2-fold and about 20-fold. In an embodiment the adipose tissue-derived cell secretions is a preparation concentrated by about 10-fold.

Without wishing to be bound by any proposed mechanism of action, it is proposed that the adipose tissue-derived cell secretions comprise cytokines, such as anti-inflammatory cytokines, that are able to migrate to a source of injury or disease and there effect improvement in the underlying condition, or alleviation of pain associated with the condition. Similarly, the adipose tissue-derived cell suspension, optionally comprising adipocytes, when injected subcutaneously or intramuscularly then operate to secrete various cell factors, such as cytokines, which are able to migrate to the site of injury or disease, be it clinical or subclinical, thereby effecting improvement of the underlying condition or prevention of clinical occurrence, for example in an intensively farmed animal. As described in the Examples herein, the method is also effective in improving lameness of a treated individual and may provide benefits in performance enhancement, as demonstrated by the improved agility and mobility of treated individuals.

Adipose Tissue

The cell secretions of the invention are adipose tissue-derived cell secretions. The cell suspensions of the invention are adipose tissue-derived cell suspensions. Adipose tissue may be human adipose tissue or mammalian animal adipose tissue. The human or animal may be alive or dead, provided that there are still viable cells within the adipose tissue. The adipose tissue may comprise "white" adipose tissue, or "brown" adipose tissue.

The adipose tissue may originate from any source in the body which is accessible. Subcutaneous fat, for example, is readily accessible with only superficial wounding, or by using "keyhole surgery" techniques. For example adipose tissue may be tissue collected using liposuction techniques, or adipose tissue which is removed with reproductive tissue when de-sexing a male or female animal. The adipose tissue may be rinsed with a tissue culture medium or buffered isotonic solution to remove adherent blood cells, and may be trimmed or coarsely processed to remove large blood vessels or connective tissue elements prior to generating an adipose tissue-derived cell suspension.

The adipose tissue may be derived from a mature or from a juvenile animal.

In particular embodiments the mammal is a companion animal, such as a canine or a feline domestic animal, or a working animal. In other particular embodiments the mammal is a, farm animal or racing animal selected from a horse, donkey, ass, cow, buffalo, sheep, goat, camel or pig.

Adipose Tissue-Derived Cell Suspension

The adipose tissue-derived cell secretions and hence the compositions comprising such secretions, are preferably prepared by first obtaining or preparing an adipose tissue-derived cell suspension. As described herein the methods, kits, uses, and compositions of the invention may comprise adipose tissue-derived cell secretions, an adipose tissue-derived cell suspension or a combination of the cell secretions and the cell suspension. The adipose tissue-derived cell suspension may or may not comprise adipocytes.

The term "adipose tissue-derived cell suspension" as used herein encompasses isolated cells from adipose tissue or small aggregates or pieces of adipose tissue, or a mixture of two or more of: isolated cells, small aggregates and pieces of adipose tissue. The cell suspension may be obtained by mechanically dissociating adipose tissue using techniques which are readily available in the art. Any suitable method for the mechanical dissociation of adipose tissue may be used, for example by mincing adipose tissue with blades, or with scissors, or by forcing adipose tissue through screens or meshes with a pore size sufficient to break the tissue into isolated cells or small pieces of adipose tissue, or a combination of these techniques. Small aggregates of adipose tissue may form when dissociated adipose-derived cells reassociate into larger assemblies, for example on standing in a medium. Small pieces or aggregates of adipose tissue may be less than ten millimeters in diameter, less than five millimeters in diameter, less than one millimeter in maximum diameter, less than 500 µm in maximum diameter or less than 250 µm in maximum diameter.

The adipose tissue-derived cell suspension may be filtered through a mesh or screen to remove cell aggregates or tissue pieces which are greater than the mesh or screen pore size.

Proteolytic enzymes may be used to promote the dissociation of adipose tissue into an adipose tissue-derived cell suspension. Enzymes which are suitable for such a use are well known in the art, and include but are not limited to trypsin, and collagenase. It is usual to remove and/or otherwise inactivate the proteolytic enzymes before using the adipose-tissue-derived cell extract, as these enzymes may not be compatible with a desired in vivo use of the cells. The proteolytic enzymes may be used in combination with techniques for the mechanical dissociation of adipose tissue to generate an adipose tissue-derived cell suspension.

A mechanical dissociation technique may be used without using one or more proteolytic enzymes. The technique used in this manner may be used to rapidly generate an adipose tissue-derived cell suspension.

The cell suspension may be suspended in a liquid. The liquid may be added to the adipose tissue before, during or after the dissociation of the adipose tissue. The liquid may comprise a medium which is capable of maintaining adipose tissue cell survival for at least 24 hours under appropriate culture conditions. The liquid may comprise an isotonic buffered solution, such as a phosphate or a HEPES buffered saline, which is capable of maintaining adipose tissue cell survival for at least one hour. The liquid may comprise a tissue culture medium. The liquid may comprise serum or serum components which support or extend adipose tissue cell survival in the cell suspension. The serum or serum components may be autologous serum or serum components.

In some embodiments the cell suspension may not have added liquid, but instead the cells are suspended in liquid which is formed during the dissociation of the tissue.

The preparation of an adipose tissue-derived cell suspension may comprise a centrifugation step. The centrifugation of isolated cells or small aggregates or pieces of adipose tissue suspended in a liquid, such as a medium, is at approximately 500 g for 10 minutes, or for sufficient time and at a sufficient g-force to generate a cell pellet which comprises adipose-derived non-adipocyte cells, above which is a layer of medium, floating above which in turn is a layer which comprises the viable adipocytes, and floating at the top is a layer of lipid which is derived from ruptured adipocytes. Following centrifugation, in certain embodiments the lipid layer and the medium layer will be discarded and the retained cells are mixed, leaving an adipose tissue-derived cell suspension which comprises viable adipocytes and adipose-derived non-adipocyte cells. In other embodiments, only the layer comprising the viable adipocytes will be retained. In other embodiments, the layer comprising adipocytes may be removed and hence not included in the adipose tissue-derived cell suspension. This will typically occur when preparing an adipose tissue-derived cell suspension which is substantially free of adipocytes. A cell suspension referred to herein as being substantially free of adipocytes means that the cell suspension has been significantly depleted of adipocytes compared to the starting material, such as by removal of the adipocyte fraction after centrifugation. It will be understood that substantially free of adipocytes when used in relation to a cell suspension includes complete absence of adipocytes and also includes the situation where minimal retention of adipocytes in the material has occurred. In other embodiments, only part of the adipocyte content of the adipose tissue may be removed in the preparation of the adipose tissue-derived cell suspension. In this case, the resultant cell suspension will comprise adipocytes, but at a reduced proportion relative to other retained components, such as the stem cells, compared to the proportion in the starting material. In an embodiment the adipose tissue-derived cell suspension comprises at least 10% adipocytes by volume. In an embodiment the adipose tissue-derived cell suspension comprises between 10% and 30% adipocytes by volume One centrifugation step or multiple centrifugation steps may be used, for example to provide additional cell separation steps. In other embodiments, the preparation of an adipose tissue-derived cell suspension does not include a centrifugation step.

The adipose tissue-derived cell suspension may or may not comprise viable adipocytes. When present, the adipocytes may retain detectable quantities of lipid in their cytoplasm, and may be separated from adipose-derived non-adipocyte cells on the basis of the different density provided by the lipid. Lipid may be detectable using light microscopy techniques, including phase contrast microscopy, or by staining a sample of cells with a lipophilic dye such as Oil Red O. Adipocytes which retain lipid in their cytoplasm are considerably more fragile than other adipose-derived cells, and accordingly where viable adipocytes are desired techniques for dissociating tissue which damage or kill a large proportion of the adipocytes should be avoided. The ultrasonic dissociation of adipose tissue or techniques in which adipose tissue is vigorously shaken, for example, are unlikely to provide a cell suspension which contains large numbers of viable adipocytes. The viability of adipocytes may readily be determined using readily available techniques, such as the LIVE/DEAD cell viability assays (Molecular Probes).

The adipose tissue-derived cell suspension may comprise both adipocytes and adipose-derived non-adipocyte cells. The adipose-derived non-adipocyte sells typically include cells of the stromal vascular fraction, including mesenchymal stem cells. Cells of the stromal vascular fraction typically pellet upon centrifugation conditions described herein of an adipose tissue-derived cell suspension.

In embodiments which comprise both adipocytes and adipose-derived non-adipocyte cells, the adipose tissue-derived cell suspension may be conveniently prepared by methods which comprise a centrifugation step, as described herein, in which both the adipocyte cell layer and the pelleted adipose-derived non-adipocyte cells are collected. Alternatively, in these embodiments the adipose tissue-derived cell suspension may be prepared by dissociating adipose tissue as described herein without a centrifugation step.

The adipose tissue-derived cell suspension, optionally comprising adipocytes, may be stored under appropriate conditions. The storage conditions typically permit the retention of cell viability of some or all cells in the cell suspension, such as greater than 50%, greater than 60%, greater than 70%, greater than 80%, greater than 90%, or greater than 95%.

Where the adipose tissue-derived cell suspension is to be stored frozen it may be in any carrier liquid appropriate for freezing of cells. As an illustrative but not limiting example, the cells may be suspended in culture medium, which may be serum-containing or serum-free, such as DMEM, RPMI, minimal essential media, or in serum prior to freezing.

Where the adipose tissue-derived cell suspension is to be stored frozen it typically also comprises a cryopreservative, for example, dimethylsulfoxide (DMSO) or glycerol, at an appropriate concentration, such as 5% to 10%. As described herein cell secretions such as those obtained or derived from cell culture of an adipose tissue-derived cell suspension can also be used as a cryopreservative for cell storage. Such secretions, optionally clarified and or optionally concentrated, can be combined with a cell population intended for frozen storage, such as mesenchymal cells, such as adipose tissue-derived cells, including a cell line resulting from culturing of an adipose tissue-derived cell suspension. The combination may be held at an appropriate temperature, such as room temperature, for example approximately 18 C to 25 C, prior to freezing for any suitable time, such as up to about one or two hours, to permit interaction between the secretions and the cells, for example approximately 10 minutes, 20 minutes, 30 minutes, 60 minutes, 90 minutes or two hours. In preferred embodiments the combination is held at room temperature for about 30 minutes.

The constituents of the cell suspension, such as the liquid medium and the cryopreservative, are typically pharmaceutically acceptable at the concentrations used. This has the advantage that the adipose tissue-derived cell suspension can be administered to a recipient subject or animal after thawing with minimal post-thaw processing.

The cell suspension is typically frozen under controlled conditions to minimize cell damage, for example by slow freezing, typically at a rate of about 1° C./min, such as by placing in a programmable freezing device, or in an insulated container in a −70° C. to −90° C. freezer. For storage, frozen cells are typically then transferred to liquid nitrogen storage.

A cell processing method and device which may be used for the preparation of adipose tissue-derived cell suspensions is described in co-pending application PCT/AU2012/000272, the contents of which are incorporated herein by reference.

Bovine Adipose Tissue Derived Cell Suspensions

The adipose tissue-derived cell suspensions, and hence the adipose tissue-derived cell secretions, may be derived from any appropriate source. Bovine adipose tissue is one such source. The inventor has previously described inventive methods for the preparation of adipose tissue derived cell suspensions from bovine sources, particularly from bovine tail base tissue, as that material was found to be refractory to standard methods appropriate to multiple other sources of adipose tissue, such as human, canine, equine, mouse and rat. This is described in co-pending application PCT/AU2012/000274, the contents of which is incorporated herein by reference.

For example, where the present invention utilises bovine adipose-derived material, a bovine adipose tissue-derived cell suspension for use as a therapeutic composition or for use in the preparation of adipose tissue-derived cell secretions may be prepared according to a method comprising:
  exposing a sample of bovine adipose tissue to a proteolytic enzyme solution to generate a cell suspension;
  centrifuging the suspension of cells to form a cell pellet, a free lipid layer above a floating cell layer which comprises adipocytes and an intermediate layer between the cell pellet and the floating cell layer, said intermediate layer being to depleted of cells relative to the cell pellet and the floating cell layer; and
  removing the free lipid layer and the intermediate layer and mixing the cell pellet and floating cell layer to form an adipose tissue derived cell suspension which comprises adipocytes.

In the methods, uses and compositions of the invention where a cell suspension which does not comprise adipocytes is desired, the floating cell layer which comprises adipocytes may also be removed and discarded in the performance of the above method.

The method may comprise additional steps in the preparation of adipose tissue-derived cell suspensions as set out elsewhere in this specification, in particular the previous section headed "Adipose Tissue-Derived Cell Suspension". These additional steps include, for example, mechanically dissociating the tissue, and suspension via a medium or buffer etc.

The removed intermediate layer may be retained as it typically includes adipose tissue-derived secretions. As the concentration of secretions in the removed intermediate layer is typically low compared to the concentration of secretions produced from subsequent cell culturing of adipose tissue-derived cell suspensions, as described below, cell secretions harvested from cultured cells are typically used in the methods, uses and compositions of the invention.

In certain embodiments the proteolytic enzyme solution comprises collagenase. The collagenase typically is used at a final concentration of about 0.2% w/v or about 0.25% w/v or greater. In certain embodiments the exposure of the bovine adipose tissue to proteolytic enzyme is conducted under conditions which result in incomplete digestion of the adipose tissue, such as which result in significant amounts of intact adipose tissue being present. Typically, for example, there may be pieces of adipose tissue present that are the same size as they were prior to starting the digestion. In embodiments of the method anywhere between about 20% to about 80% of the adipose tissue may not be digested.

In certain embodiments the cells may be subjected to multiple centrifugation steps or wash steps, for example in order to remove excessive free lipid.

As described further in the following section an adipose tissue-derived cell suspension which may be of any species origin, such as mentioned herein, for example bovine, porcine, canine, feline, equine, human, etc, or an aliquot thereof, may be used in the preparation of a composition comprising secretions of the adipose tissue-derived cells.

Compositions Comprising Adipose Tissue-derived Secretions

A composition comprising secretions from adipose tissue-derived cells may be prepared from an adipose tissue-derived cell suspension by any appropriate manner. As noted herein the liquid components formed during the preparation of an adipose tissue-derived cell suspension typically includes adipose tissue-derived secretions, thereby representing one embodiment of a composition comprising such secretions. In this form the composition comprising adipose tissue-derived secretions may be collected at any appropriate stage in the preparation of a cell suspension, such as by collection of the intermediate liquid layer between the cell pellet and the floating cell layer after centrifugation of the adipose tissue-derived material. In this embodiment the collected material comprising secretions may or may not include adipocytes.

Typically, the composition is generated by exposure of a medium to the adipose tissue-derived cell suspension comprising adipocytes. Exposure of the medium to the adipocyte tissue-derived cell suspension may be for any appropriate time and conditions, as set by the operator. Exposure of the medium to the adipocyte tissue-derived cell suspension does not require conditions which enable cell attachment to a substratum. In these embodiments, the composition comprising adipose tissue-derived secretions may be generated by exposing a medium to the adipose tissue-derived cell suspension for any appropriate period of time, such as at least 6 hours, at least 8 hours, at least 10 hours, or at least 12 hours, followed by removal of the cell suspension from the medium, or vice versa, for example by centrifugation or by filtration. In an embodiment, the adipose tissue-derived cell suspension may be exposed to low oxygen conditions, such as less than 10% oxygen, less than 5% oxygen or less than 1% oxygen. The removal of the cell suspension and the medium from each other may result in complete or incomplete removal of cells. Hence the medium, which comprises the adipose tissue-derived secretions, may or may not include adipocytes after removal from the cell suspension. In certain embodiments the composition is generated by exposing a medium to the adipose tissue-derived cell suspension for no more than 12 hours, no more than 18 hours or no more than 24 hours. In certain embodiments the composition may be generated by exposing a medium to the adipose tissue-derived cell suspension for a longer period of time, such as any period of time between about 1 and 15 days, for example for about 1 day, 2 days, 3 days, 4, days, 5 days, 6 days, 7 days, 8 days, 9 days, 10 days, 11 days, 12 days, 13 days, 14 days or 15 days. Typically, the suspension is kept in an incubator for 5 to 10 days and then the secretions are collected. Exposure of the medium to the cells may or may not be under conditions which enable cell attachment to a substratum. Typically, where exposure of the medium to the cells is for more than about 1 day the conditions will permit cell attachment to the substratum.

The composition may comprise cell-derived molecules which are released from cells following cell death or the breakup of adipose tissue cells. The composition may comprise secretions of cells of the adipose tissue-derived cell suspension, optionally comprising adipocytes. The exposing of a medium to an adipose tissue-derived cell suspension may be at a temperature of from 4° C. to 50° C., more typically at a temperature of from 10° C. to 40° C. and most typically at a temperature of from 20° C. to 37° C.

For a typical adipose tissue-derived cell suspension, 5 g of adipose tissue is dissociated and suspended in 50 mls of DMEM containing 10% autologous serum. The adipose tissue derived cell suspension typically comprises from 100,000 to 1,000,000 non-adipocyte cells for every gram of adipose tissue source material. The number of adipocytes per gram of adipose tissue source material is typically between 100,000 and 5,000,000.

The term "medium" as used herein is intended to encompass compositions which support the survival of at least some cells in an adipose tissue-derived cell suspension for at least one hour. The medium may be a tissue culture medium, such as DMEM, RPMI, or minimal essential medium, optionally supplemented with serum. The medium may be a buffered isotonic solution, such as a phosphate buffered saline or Hank's buffered saline solution, provided the medium is suitable for administration to a subject. The medium may be liquid which is formed during the dissociation of adipose tissue. The medium may optionally be supplemented with factors which promote cell survival or attachment and cell division, such as insulin, progesterone and selenium, or serum or serum components. In certain embodiments the medium must be suitable for a pharmaceutical composition, which is acceptable for in vivo use. Such media will be substantially free of pyrogens or other impurities which may be harmful to humans or animals. Pharmaceutically-acceptable media are commercially available. The phrase "pharmaceutically acceptable" refers to molecular entities and compositions that do not produce unacceptable adverse, allergic, or other untoward reactions when administered to an animal or a human.

Preparation of a composition comprising adipose tissue-derived secretions may include a step of lysis of the adipose tissue-derived cell suspension comprising adipocytes. A lysate comprising cell secretions may be prepared by any suitable method. In an example embodiment, an adipose tissue-derived cell suspension may be exposed to a medium, such as described above. Cells of the suspension may then be lysed by any suitable means, such as by mechanical disruption (eg, vigorous shaking or agitation), ultrasonic disruption, freeze thawing, freeze drying or the addition of one or more agents capable of inducing cell lysis, typically adipocyte lysis. Such lysing agents are known in the art and include urea, sodium dodecyl sulphate and Triton ×100. After a lysis step the preparation may be centrifuged or filtered to assist in the removal of cell debris, or it may be used without such a clarifying step, in which case the composition comprising adipose tissue-derived secretions may also include cell debris. In some cases the cell lysate may be removed from the lysing agent by precipitation of the cell lysate. Where the lysis step results in incomplete cell lysis, the composition comprising adipose tissue-derived secretions may also comprise adipose-derived cells, such as adipocytes.

In certain embodiments preparation of the adipose tissue-derived secretions comprises culturing the cell suspension comprising adipocytes under appropriate conditions to form an adherent cell culture, such as a confluent adherent cell culture; harvesting supernatant of the adherent cell culture and removing cells from said supernatant to form a composition comprising adipose tissue-derived secretions. The removal of the cells from the supernatant to leave a composition comprising adipose tissue-derived secretions may be complete removal or may be partial removal. In the latter case, the composition comprising adipose tissue-derived secretions may therefore also include adipocytes.

Prior to commencing the culturing of the cells, the adipose tissue derived cell suspension may be re-suspended in a desired volume of an appropriate buffer, such as DMEM, RPMI or minimal essential media. The cell suspension, or an aliquot thereof, may be added to a sterile tissue culture flask and incubated under appropriate conditions, typically until the adherent cells have reached confluence. The cell culture is preferably in the presence of sterile serum. The concentration of the serum in the culture may be any suitable concentration which assists culturing of adipose tissue-derived cells, such as for example in the range of about 5% v/v to about 30% v/v, such as about 10% v/v, or about 15% v/v or about 20% v/v. The serum may be any appropriate serum for the culturing of adipose tissue-derived cells, such as a commercial fetal calf serum, or a serum prepared in house, such as by methods known in the art. The serum may be autologous, having been prepared from the same individual from which the adipose tissue was obtained, or it may be allogeneic. In other embodiments the serum may be xenogeneic, such as the use of calf serum in the culturing of adipose tissue-derived cells obtained from a canine source. Typically, the cells are cultured at 37° C. with 5% $CO_2$. In a further embodiment the cells are cultured in hypoxic conditions.

During culturing the adipose tissue-derived cells secrete cytokines including anti-inflammatory molecules, pro-inflammatory molecules, chemokines, growth factors and other cell signalling molecules into the medium. The supernatant in the culture thereby comprises adipose tissue-derived secretions.

In certain embodiments the culture may be frozen and freeze dried, resulting in a freeze dried preparation that includes cells and the secretions. Rehydration of the freeze dried preparation will lyse the majority of the cells resulting in the release of additional cytokines. Rehydration will typically be performed using a volume of fluid that is less than the original volume of the adipose tissue-derived cells, such as a volume of fluid that is between about 5 and about 20 times less than the original volume, more typically about 10 times less than the original volume of the adipose tissue-derived cells which results in a composition that is 10 times concentrated. The composition may then be filtered to remove cell debris resulting in a composition that contains concentrated cytokines. This provides a preferred method for producing large volumes of concentrated secretions.

In other certain embodiments the supernatant may be harvested from the culture at any appropriate time, although typically for an adherent cell culture it will be harvested when the cells have reached confluence, such as after about 3, 4, 5, 6, 7, 8, 9, 10, 11, 12, 13 or 14 days. Cells, cell debris and any remaining adipose tissue may be removed from the supernatant, such as by filtration. In an embodiment the filtration may be through a 20 micron mesh. If desired, multiple steps of filtration may be undertaken such as through two or more filters of decreasing mesh size. The resultant preparation of adipose tissue-derived secretions is typically filter sterilised, such as through a 0.22 micron filter. The sterilised composition may be used immediately, or may be aliquoted for use, or for storage. Typically, if stored, the composition is stored frozen at −20° C. The composition contains secretions from the adipose tissue-derived cells.

A composition comprising adipose tissue-derived secretions may also comprise adipocytes. Where present, the adipocytes may remain from the original adipose tissue used in the preparation of the secretions or they may be added to the composition comprising the secretions.

As described above the preparation of adipose tissue-derived cell secretions may be made by culturing an adipose tissue-derived cell suspension and subsequent harvest and filtration of supernatant, with or without additional steps described above, such as filter-sterilizing, freeze-drying and concentrating.

A composition comprising the secretions, which may be a harvested supernatant comprising secretions, may, for example, be freeze-dried and subsequently re-hydrated in a desired volume of an appropriate liquid. Typically the appropriate liquid will be pharmaceutically acceptable. The appropriate liquid may be distilled water.

Optionally, confluent adipose tissue-derived cell cultures, after harvest of supernatant, may be passaged into new tissue culture flasks and cultured again to confluence under appropriate conditions. Continued passaging of the cells may be undertaken for the preparation of adipose tissue-derived secretions. For example, supernatant may be harvested from flasks in any desired passage number, for example from flasks in passage number three through to passage five. Harvested supernatants may be pooled as desired, for example to obtain a greater amount of secretions. With additional steps, such as concentration steps, in this manner an adipose tissue-derived cell secretion preparation of higher concentration may be prepared.

Pharmaceutical Compositions and Other Compositions of the Invention

In aspects of the invention the adipose tissue-derived composition, containing secretions of adipose tissue cells, or the adipose tissue-derived cell suspension, optionally comprising adipocytes, is used for the preparation of a pharmaceutical composition. According to one aspect the invention provides (i) a composition comprising adipose tissue-derived secretions or (ii) an adipose tissue-derived cell suspension, optionally comprising adipocytes or (iii) a combination of (i) and (ii) for the preparation of a pharmaceutical composition for use in the treatment of a condition selected from the group consisting of an inflammatory disorder, a ligament injury and a tendon injury in a subject, or for use in alleviating pain associated with an inflammatory disorder, a ligament injury; a tendon injury, neuropathic pain, or a burn injury, wherein the treatment comprises remote administration of the pharmaceutical composition to the subject. The pharmaceutical composition may also be referred to as a medicament.

Typically, the remote administration is subcutaneous administration or intra-muscular administration. Typically the pharmaceutical composition also comprises one or more of a pharmaceutically acceptable carrier diluent, excipient or adjuvant.

In another aspect the invention provides use of (i) a composition comprising adipose tissue-derived secretions or (ii) an adipose tissue-derived cell suspension, optionally comprising adipocytes, or (iii) a combination of (i) and (ii), for the preparation of a pharmaceutical composition for use in the treatment or prevention of disease in an intensively farmed animal, wherein the pharmaceutical composition is suitable for subcutaneous injection or intramuscular injection.

In another aspect the invention provides use of use of (i) a composition comprising adipose tissue-derived cell secretions, or (ii) an adipose tissue-derived cell suspension, optionally comprising adipocytes, or (iii) a combination of (i) and (ii), for the preparation of a pharmaceutical composition for use in the treatment of a joint disease or condition in a mammalian subject, wherein the composition is suitable for administration to a site of said subject remote from the site of said condition.

In another aspect the invention provides use of (i) adipose tissue-derived cell secretions, or (ii) an adipose tissue-derived cell suspension, optionally comprising adipocytes, or (iii) a combination of (i) and (ii), for the preparation of a pharmaceutical composition for use in alleviating pain in a mammalian subject, wherein the pharmaceutical composition is suitable for administration to said subject by intramuscular injection or by subcutaneous injection or by an appropriate form of administration, such as by topical administration, at or near a site of the pain.

The invention thus provides pharmaceutical compositions or medicaments comprising (i) adipose tissue-derived cell secretions, or (ii) an adipose tissue-derived cell suspension, optionally comprising adipocytes, or (iii) a combination of (i) and (ii). The pharmaceutical composition may be provided as part of a kit, for example including additional components useful in the intended treatment, such as for example written instructions, or it may be provided as a single item, such as a single vial or aliquot of the composition.

According to a further aspect the invention provides a pharmaceutical composition comprising adipose tissue-derived secretions, together with a pharmaceutically acceptable carrier, diluent, excipient or adjuvant. In certain embodiments the composition comprising adipose tissue-derived secretions further comprises adipocytes. In certain embodiments the composition is cell-free. In certain embodiments the composition is prepared by exposing a medium or other liquid to an adipose tissue-derived cell suspension, which may or may not comprise mature adipocytes. The pharmaceutical composition has therapeutic properties, such as for the treatment of a condition selected from the group consisting of an inflammatory disorder, a ligament injury and a tendon injury in a subject, or for alleviating pain associated with a condition selected from the group consisting of an inflammatory disorder, a ligament injury, a tendon injury, neuropathic pain and a burn injury. The pharmaceutical composition has therapeutic properties suitable for treatment or prevention of disease in an intensively farmed animal. Such diseases include leg weakness, lameness, arthritis, developmental diseases and bacterial infection. In an embodiment the developmental disease is osteochondrosis (OCD). In an embodiment the developmental disease is a bone cyst. In an embodiment the developmental disease is an orthopaedic developmental disease.

In embodiments, the adipose tissue is taken from an individual subject, and the pharmaceutical composition is administered to the same individual, and thus the adipose tissue-derived secretions or adipose tissue-derived cell suspension, optionally comprising adipocytes, or combination thereof, is a purely autologous preparation.

In embodiments, the adipose tissue is taken from one or more individual subjects and the pharmaceutical composition is administered to a different subject of the same species, and thus the adipose tissue-derived secretions or adipose tissue-derived cell suspension, optionally comprising adipocytes, or combination thereof is an allogeneic preparation. In embodiments the adipose tissue is taken from an individual of a different species to that which is intended to be a recipient of the therapeutic composition. For example, a composition comprising secretions or cells or a combination of both prepared from bovine tissue may be for administration to an individual of a different species, such as a human, feline, porcine, or canine. In embodiments where the composition comprising adipose tissue-derived secretions or adipose tissue-derived cell suspension, optionally comprising adipocytes, is for use in a different individual of the same species as the source material or for use in an individual of a different species as the source material, the composition may typically be devoid of cells of the immune system in order to minimise the possibility of host (recipient) immune response to the composition or graft versus host disease.

In embodiments the pharmaceutical composition is prepared from more than one source of adipose tissue, such as from different preparations taken from the same individual or from different preparations taken from different individuals. The pooling may comprise combining multiple adipose tissue-derived cell suspensions, such as in a pooled culturing step or the pooling may comprise combining multiple compositions of adipose tissue-derived secretions, such as may be obtained from separate culturing or exposure steps.

The pharmaceutical composition may be administered to the subject patient at a site remote from the afflicted area. In this context, "remote" means that the administration is not direct application of the cell secretions or cell suspension or combination thereof to the site of inflammation or other injury or disease being treated where such a site is identifiable. As an illustration, in the case of treatment of an arthritic joint, administration as previously described in the art involved injection of adipose tissue-derived cell suspensions or adipose tissue-derived cell secretions directly into the afflicted joint. Such administration requires a high degree of skill on the part of the treating physician or clinician to ensure appropriate precision. The handling of the affected limb or joint required in such administration also increases the distress experienced by the patient, be they human or non-human. By providing for the remote administration of adipose tissue-derived cell secretions, or adipose tissue-derived cell suspension, or combination thereof, the present invention offers improved methods, uses and compositions for the treatment of such diseases. For example, the remote administration may be by subcutaneous injection, such as in the scruff of the neck of an animal (for example a cat or dog) being treated, or by intramuscular injection. As a further example, administration to a dog by intramuscular injection may be in to thigh of the dog. As a further example, administration to a bovine by intramuscular injection may be in the caudal fold.

Where the therapeutic compositions of the invention are administered to treat or prevent a disease of an intensively farmed animal, the administration is by subcutaneous injection or intramuscular injection. Due to the nature of the condition being treated in such an animal description of the administration being "remote" may not be appropriate. For example, administration of the therapeutic composition of the invention to an intensively farmed animal may be for treatment or prevention of generalized or localized leg weakness, osteochondrosis. As described herein administration of the therapeutic composition to such animals is by subcutaneous injection or intramuscular injection.

Where the therapeutic compositions of the invention are administered for treatment of pain for which there is no discernable clinical cause, or for neuropathic pain which may or may not have a discernable clinical cause, the composition may be administered to the subject by any appropriate means, such as by injection or by topical application, which means may be at or near a site of the pain or may be remote from a site of the pain. Neuropathic pain may be experienced by a subject at multiple sites in the body. Treatment of such pain may be by administration at one site, such as a site of original pain, which site may also be remote from another site of pain experienced by the subject. In an example, the pain is neuropathic pain. The neuropathic pain may be localised to one area of the body or it may be experienced in multiple sites of the subject's body. When experienced in multiple sites, the intensity of the pain may be similar at multiple sites or it may be different at multiple sites. An example of neuropathic pain is neuropathic facial pain. In methods of the invention, neuropathic facial pain in a subject may be treated by administration of a composition of the invention to the subject by injection into the jaw or the gum. The injection into the jaw or the gum of such a patient may comprise administration at the original site of the pain or may be administration at a secondary site of the pain.

As shown in the Examples compositions and methods of the invention are also effective in alleviating pain and blistering associated with burns. Where the compositions of the invention are administered for treatment of a burn injury, or for alleviating pain associated with a burn of the skin, the composition is typically administered by topical application, such as in the form of a cream, gel, or lotion.

A pharmaceutical composition of the invention may be supplied to the user as a frozen solution. As described herein, for example, the cell secretions, the cell suspension, or the combination can be stored, at approximately −20° C. until required for use. Alternatively, the cell secretions, the cell suspension, or the combination may be stored at a lower temperature, for example in a freezer at −70° C. to −90° C., or in liquid nitrogen storage, either in the vapour phase or in the liquid phase, until required for use. Compositions comprising cells will typically be stored in liquid nitrogen. In a preferred embodiment the composition comprising adipose tissue-derived cell secretions, or the adipose tissue-derived cell suspension, optionally comprising adipocytes, or the combination of adipose tissue-derived cell secretions and adipose tissue-derived cell suspension, optionally comprising adipocytes, is stored in the liquid phase of liquid nitrogen storage. In a preferred embodiment a composition comprising cells is stored in combination with cell secretions obtained from a culture of adipose tissue-derived cells. In another preferred embodiment a composition comprising cells is stored in a composition which comprises clarified and or concentrated media from a culture of adipose tissue-derived cells. The culture of adipose tissue-derived cells will be understood to include culture of cells freshly obtained from adipose tissue, as well as culture of cells which have arisen as progeny cells or a cell line from prior culturing. In use, such as by the treating physician, clinician, veterinarian, technician, assistant, or farmer, the composition is typically administered to the subject or animal as soon as possible after thawing. The pharmaceutical composition may alternatively be stored, for example on ice or in a refrigerator or in a cool pack, at approximately 2° C. to 5° C. for a short time between thawing and administration. In this context a short time would typically be no more than several hours, such as no more than about half an hour, or no more than about one hour, or no more than about two hours. As the cryoprotectants are typically toxic to the cells and can cause loss of viability if kept thawed, the composition, particularly where it comprises viable cells, is typically injected to the recipient animal as soon as possible after thawing.

It had previously been considered that a stored (eg., a frozen) suspension comprising mesenchymal stem cells requires a period of time under appropriate cell culturing conditions before use in a therapeutic setting, for example to assist in cell recovery. The inventor has surprisingly identified that culturing of a previously frozen cell suspension, such as an adipose tissue-derived cells suspension optionally comprising adipocytes, is not required prior to use of the cell suspension in a therapeutic setting. As described herein benefits from the administration of such a cell suspension are apparent when the cell suspension is administered after thawing and without intervening cell culturing. As demonstrated in the Examples herein, storage of cells in the presence of adipose tissue-derived cell secretions provides further benefits. For example, frozen cells stored in the presence of secretions, optionally a clarified and or concentrated preparation of secretions, demonstrate superior therapeutic efficacy when utilised after retrieval from storage compared to frozen cells stored in the absence of secretions.

A pharmaceutical composition of the invention may be supplied in a "ready-to-use" form. In such embodiments the user typically requires only thawing to an acceptable temperature for administration before the composition is administered. In such embodiments the composition may be supplied in pre-measured doses, such as a pre-measured or pre-determined dose suitable for a given recipient subject or animal, for example pre-determined on the basis of the recipient species, or on the basis of the recipient individual, such as a small breed of dog, compared to a large breed of dog, or a juvenile animal compared to an adult animal. The pre-measured dose may alternatively or additionally be on the basis of the disease or condition being treated or intended to be prevented. A ready-to-use form of the composition may comprise the composition supplied with or in an injectable device, such as a syringe. The injectable device may be capable of delivering a single application to an individual recipient or may be capable of delivering single or multiple applications to multiple recipients. The injectable device may be adjustable, for example to permit delivery of a range of different doses.

In embodiments where the pharmaceutical composition comprises a combination of adipose tissue-derived cell secretions and an adipose tissue-derived cell suspension, optionally comprising adipocytes, the composition may be supplied to the user as a combination or as separate compositions for combination by the user. It will be understood that reference to a "user" in this context means the individual who actually administers the therapeutic composition to the recipient subject or animal and also means a member of the team or group who is undertaking that administration. For example the user may be any individual who is assisting in the application of the methods of the invention such as a clinician, a doctor, a veterinarian, a farmer, a clinical nurse, a veterinary nurse, a technical assistant, or a farmhand.

Inflammatory Disorders

The pharmaceutical composition may be administered for the treatment of an inflammatory disorder and/or for alleviating pain associated with an inflammatory disorder in a subject.

Inflammation may arise as a response to an injury or abnormal stimulation caused by a physical, chemical, or biologic agent. An inflammation reaction may include the local reactions and resulting morphologic changes, destruction or removal of the injurious material, and responses that lead to repair and healing. The term "inflammatory" when used in reference to a disorder refers to a pathological process which is caused by, resulting from, or resulting in inflammation that is inappropriate or which does not resolve in the normal manner. Inflammatory disorders may be systemic or localized to particular tissues or organs.

Inflammation is known to occur in many disorders which include, but are not limited to: Systemic Inflammatory Response (SIRS); Alzheimer's Disease (and associated conditions and symptoms including: chronic neuroinflammation, glial activation; increased microglia; neuritic plaque formation; and response to therapy); Amyotropic Lateral Sclerosis (ALS), arthritis (and associated conditions and symptoms including, but not limited to: acute joint inflammation, antigen-induced arthritis, arthritis associated with chronic lymphocytic thyroiditis, collagen-induced arthritis, juvenile arthritis; rheumatoid arthritis, osteoarthritis, prognosis and *streptococcus*-induced arthritis, spondyloarthopathies, gouty arthritis), asthma (and associated conditions and symptoms, including: bronchial asthma; chronic obstructive airway disease; chronic obstructive pulmonary disease, juvenile asthma and occupational asthma); cardiovascular diseases (and associated conditions and symptoms, including atherosclerosis; autoimmune myocarditis, chronic cardiac hypoxia, congestive heart failure, coronary artery disease, cardiomyopathy and cardiac cell dysfunction, including: aortic smooth muscle cell activation; cardiac cell apoptosis; and immunomodulation of cardiac cell function; diabetes and associated conditions, including autoimmune diabetes, insulin-dependent (Type 1) diabetes, diabetic periodontitis, diabetic retinopathy, and diabetic nephropathy); gastrointestinal inflammations (and related conditions and symptoms, including celiac disease, associated osteopenia, chronic colitis, Crohn's disease, inflammatory bowel disease and ulcerative colitis); gastric ulcers; hepatic inflammations such as viral and other types of hepatitis, cholesterol gallstones and hepatic fibrosis, HIV infection and associated conditions, including degenerative responses, neurodegenerative responses, and HIV associated Hodgkin's Disease, Kawasaki's Syndrome and associated diseases and conditions, including mucocutaneous lymph node syndrome, cervical lymphadenopathy, coronary artery lesions, edema, fever, increased leukocytes, mild anemia, skin peeling, rash, conjunctiva redness, thrombocytosis; inflammatory disorders of the skin, including dermatitis, such as atopic dermatitis and associated conditions; multiple sclerosis, nephropathies and associated diseases and conditions, including diabetic nephropathy, endstage renal disease, acute and chronic glomerulonephritis, acute and chronic interstitial nephritis, lupus nephritis, Goodpasture's syndrome, hemodialysis survival and renal ischemic reperfusion injury, neurodegenerative diseases and associated diseases and conditions, including acute neurodegeneration, induction of IL-I in aging and neurodegenerative disease, IL-I induced plasticity of hypothalamic neurons and chronic stress hyperresponsiveness, ophthalmopathies and associated diseases and conditions, including diabetic retinopathy, Graves' ophthalmopathy, and uveitis, osteoporosis and associated diseases and conditions, including alveolar, femoral, radial, vertebral or wrist bone loss or fracture incidence, postmenopausal bone loss, mass, fracture incidence or rate of bone loss, otitis media (adult or paediatric), pancreatitis or pancreatic acinitis, periodontal disease and associated diseases and conditions, including adult, early onset and diabetic; pulmonary diseases, including chronic lung disease, chronic sinusitis, hyaline membrane disease, hypoxia and pulmonary disease in SIDS; restenosis of coronary or other vascular grafts; rheumatism including rheumatoid arthritis, rheumatic Aschoff bodies, rheumatic diseases and rheumatic myocarditis; thyroiditis including chronic lymphocytic thyroiditis; urinary tract infections including chronic prostatitis, chronic pelvic pain syndrome and urolithiasis, immunological disorders, including autoimmune diseases, such as alopecia aerata, autoimmune myocarditis, Graves' disease, Graves ophthalmopathy, lichen sclerosis, multiple sclerosis, psoriasis, systemic lupus erythematosus, systemic sclerosis, thyroid diseases (e.g. goitre and struma lymphomatosa (Hashimoto's thyroiditis, lymphadenoid goitre), sleep disorders and chronic fatigue syndrome and obesity (non-diabetic or associated with diabetes), resistance to infectious diseases, such as Leishmaniasis, Leprosy, Lyme Disease, Lyme Carditis, malaria, cerebral malaria, meningitis, tubulointerstitial nephritis associated with malaria), which are caused by bacteria, viruses (e.g. cytomegalovirus, encephalitis, Epstein-Barr Virus, Human Immunodeficiency Virus, Influenza Virus) or protozoans (e.g., *Plasmodium falciparum*, trypanosomes), response to trauma, including cerebral trauma (including strokes and ischemias, encephalitis, encephalopathies, epilepsy, perinatal brain injury, prolonged febrile seizures, SIDS and subarachnoid hemorrhage), low birth weight (e.g. cerebral palsy), lung injury (acute hemorrhagic lung injury, Goodpasture's syndrome, acute ischemic reperfusion), myocardial dysfunction, caused by occupational and environmental pollutants (e.g. susceptibility to toxic oil syndrome silicosis), radiation trauma, and efficiency of wound healing responses (e.g. burn or thermal wounds, chronic wounds, surgical wounds and spinal cord injuries), septicemia, hypothyroidism, oxygen dependence, cranial abnormality, early onset menopause, a subject's response to transplant (rejection or acceptance), acute phase response (e.g. febrile response), general inflammatory response, acute respiratory distress response, acute systemic inflammatory response, wound healing, adhesion, immunoinflammatory response, neuroendocrine response, fever development and resistance, acute-phase response, stress response, disease susceptibility, repetitive motion stress, tennis elbow, ligament and tendon problems, and pain management and response.

In particular embodiments the inflammatory disorder is a joint-related inflammatory disorder, such as arthritis.

The methods and compositions of the invention may be used for the treatment of ligament injuries and tendon injuries or for the alleviation of pain associated with such injuries. Ligament injuries and tendon injuries, in some forms, can be classified as inflammatory disorders. Some ligament injuries and tendon injuries may not be considered inflammatory disorders. For the avoidance of doubt, ligament injuries and tendon injuries contemplated in this invention may be those which are inflammatory disorders or are associated therewith and those which may not be considered inflammatory disorders.

The methods and compositions of the present invention may be used in conjunction with other treatments, such as those for inflammatory diseases. As demonstrated in Australian Patent Application No. 2009201915 and in International Publication No. WO2010/020005, the contents of which are incorporated herein by cross-reference, administration of a composition comprising adipose tissue-derived cells, which composition comprises adipocytes, directly into an joint affected by inflammatory diseases, such as osteoarthritis, provides therapeutic benefits for the patient and is associated with improvement in the joint. The present invention additionally offers an adjunct treatment, whereby, for example, a treatment regime may be commenced by administration of the composition comprising adipose tissue-derived cells, which composition comprises adipocytes, into the affected joint, and that is followed by the less invasive course of treatment utilising the remote delivery of the present invention.

The present invention may also offer advantages as an adjunct treatment for arthritis and other inflammatory diseases in combination with established treatments. For example, a side-effect of long term treatment of inflammatory conditions utilising NSAIDS is renal failure. The present invention offers an alternative to continued use of NSAIDS in patients with signs of renal failure. Alternatively, the use of the present invention in combination with NSAIDS may permit the NSAIDS to be used at a reduced dosage, thereby delaying the onset of renal failure.

The present invention may be used in combination with any therapy known for inflammatory diseases, including use with any of cartrophen, metacam, previcox, tramadol. The methods and compositions of the present invention may be used in conjunction with herbal medications, such as valerian, rosemary oil and yucca leaves.

The present invention permits the preparation of cell secretions in advance, such that a product comprising the adipose tissue-derived cell secretions may be made available without the need to anesthetize a subject for extraction of adipose tissue. The present invention permits the preparation of compositions comprising (i) adipose tissue-derived cell secretions, or (ii) an adipose tissue-derived cell suspension, optionally comprising adipocytes, or (iii) a combination of (i) and (ii), in advance of a treatment need. As described herein the cell secretions or other compositions of the invention can be stored, for example at −20° C. or below, until required for use.

Intensively Farmed Animals

As a result of intensive selection of farm animals over many generations for desirable traits, such as rapid growth, large muscle mass and efficient feed conversion in animals raised for meat production (eg., pigs and cattle) and milk quality and volume in dairy animals, modern breeds of farm animals often have a higher prevalence of susceptibility to disease and acute and chronic conditions than do wild or less intensively farmed populations. The incidence of and severity of manifestation of such diseases and conditions can be exacerbated by the manner in which an animal is farmed. Animals raised under intensive farming conditions, such as in densely populated piggeries or in feed lots are typically susceptible to a higher incidence of disease and potentially detrimental growth conditions than animals raised under less intensive conditions, such as a free range or open grazing situation. Due to intensive selection, as described above however, even animals raised in free range or open grazing operations may still have a higher susceptibility to or prevalence of detrimental health conditions. In the context of the invention therefore it will be understood that reference to intensively farmed animals or intensive farming conditions includes intensively bred animals which may be raised in densely populated operations, for example with limited availability for individual movement, and also includes intensively bred animals in less densely populated operations, such as where an individual has access to free range or open grazing.

The identification by the inventor that the therapeutic compositions of the invention are effective when administered subcutaneously or intramuscularly is conducive to the methods and compositions of the invention having beneficial effects in farming operations and particularly intensive animal farming, such as intensive farming of pigs, cattle, sheep and poultry. Whilst a therapeutic agent for a localized disease, such as an arthritic joint, can be administered by intra-articular injection into the afflicted joint, such administration requires a high degree of skill on the part of the operator, as well as potentially causing pain to the animal by handling of the afflicted joint, and hence requiring restraint of the animal being treated. In contrast, subcutaneous injection or intramuscular injection has a lower skill requirement on the part of the operator, will generally not require handling of the afflicted limb, and typically requires only minimal restraint of the animal being treated. With the absence of requirement for high degree of operator skills, as compared to intra-articular injection for example, administration of the compositions of the invention can be undertaken as part of a routine on-farm treatment or preventive program. In such an approach animals may be administered the compositions of the invention at the same time as the animals are being treated for other conditions, or at the same time as the animals are undergoing routine procedures associated with the animal breeding or growing enterprise, such as vaccination, ear tagging, tattooing, tail docking, or castration.

Generations of selectively breeding animals of a particular species for a desirable trait has contributed to the increased prevalence of certain undesirable characteristics in the population. As an example, pigs have for many years been selected for rapid growth, large muscle mass and efficient feed conversion. This has, however, led to much greater prevalence of skeletal, joint and cartilage problems than is seen in a wild population. These problems can be exacerbated in a farming operation where the animal has limited room to move. Changes associated with cartilaginous structures may be referred to as leg weakness or osteochondrosis (OCD). The term "leg weakness" is also sometimes used to describe poor leg conformation or to describe a clinical condition associated with lameness or stiffness. It may arise due to abnormal changes in the articular cartilage and the growth (epiphyseal) plates, which are responsible for the growth of bones both in length and diameter. The exact mechanisms that cause these changes are not fully understood. They are thought to arise due to the pressure and sheer stresses that are placed upon these rapidly growing tissues, which reduces oxygen supply causing abnormal growth and consistency of the cartilage. Reduced blood supply through a deficiency of blood vessel is although thought to contribute to such problems. Damage to the cartilage tends to be progressive and irreversible, the damaged cartilage being replaced by fibrous tissue.

Shortening and bending of the bones near the joints and at extremities of long bones may follow the cartilage damage. Weak epiphyseal plates also have a tendency, to fracture and cartilage covering the joint surfaces may split and form fissures. In modern pigs, such changes in the cartilage take place from as early as two months of age. These potentially detrimental changes are not generally clinically apparent at an early stage. In breeding enterprises it is not uncommon for 20% to 30% of boars and gilts to be culled due to leg weakness and leg deformities. Such conditions, including OCD, thus have the potential for serious economic and ethical consequences for the fanning enterprise. There is currently no specific treatment for OCD. In advanced stages OCD may also lead to arthritis and permanent lameness.

The compositions of the present invention are beneficial in the growth and repair and maturation of bone and cartilage. Accordingly, the present invention provides methods for treatment or prevention of bone and cartilage disorders in an animal, including leg weakness or OCD. As OCD can lead to arthritis in an affected animal, the methods and compositions of the invention can also be effective in preventing the occurrence of or reducing the severity or incidence of arthritis in an animal at risk of arthritis. In preferred embodiments the animal is a pig. As described above, such conditions commence at an early age and, in early stages of development are typically not associated with any clinical symptoms. In the methods of the invention the therapeutic composition may be administered to an animal which exhibits clinical symptoms of a joint disease or to an animal which does not exhibit clinical symptoms of a joint disease.

Clinical symptoms may include separation or fracture of the bones at the epiphyseal plate (epiphyseolysis) associated with sudden movement, lameness, sudden fractures (such as of the knee and elbow joints) which may be more common in young animals, abnormal leg conformation, abnormal gait, stiffness, pain. Age of visible onset of OCD can be variable, for example within three months of gilts being introduced on to a farm, during the first pregnancy, in lactation or in the first two to three weeks post weaning.

In an embodiment the invention provides a method for reducing the severity of OCD in an animal, the method comprising administering to said animal a pharmaceutical composition comprising (i) adipose tissue-derived cell secretions, or (ii) an adipose tissue-derived cell suspension, optionally comprising adipocytes, or (iii) a combination of (i) and (ii), wherein the administering is by subcutaneous injection or intramuscular injection. In preferred embodiments the animal is a pig.

Administration of the pharmaceutical composition to the recipient animal may occur when the animal is at any suitable age. For prevention of the onset of clinical symptoms of OCD or for reducing the severity of OCD in a pig, the recipient is preferably treated at a young age. For example a pig may be treated at, or soon after weaning, which typically occurs in a pig farming operation when the piglets are between about two and five weeks old. Young pigs may be treated at between about one month and six months of age; or between about three months and six months of age. In piggeries, the pigs undergo a rapid growth phase at about 12 to 16 weeks of age. It is envisaged that in one embodiment the administration of the compositions of the invention would be at the beginning of this growth period, for example at around 8 weeks of age, or 9 weeks of age, or 10 weeks of age, or 11 weeks of age, or 12 weeks of age, or 13 weeks of age.

The animal may receive a single administration of the composition of the invention or may receive multiple administrations, such as two, three, four or more administrations. Where multiple administrations of the composition are performed, they will typically be separated by about one, two, three or four months in the case of administration to young pigs.

The method is also beneficial in the treatment of symptomatic OCD. In such cases the recipient animal is typically an older animal, such as more than six months old. In an older animals multiple administration of the compositions of the invention may be separated by about two to six weeks, or by about one, two, three or four months or more. The choice of timing of multiple administration may be determined by the skilled addressee, for example it may be on the basis of re-appearance of or increased severity of symptoms, pregnancy, weaning, etc.

As described above the compositions and methods of the invention find application in preventing onset of OCD in pigs and in reducing the severity of OCD and other developmental orthopaedic conditions in pigs. Other mammals including humans, dogs, cattle, and horses, may also suffer developmental orthopaedic conditions, such as OCD, for example through predisposition due to environment and or genetics. The invention also finds application in preventing onset of, or the severity of, or in treating, developmental orthopaedic conditions, such as OCD, in such animals.

As described herein the compositions of the invention are also capable of treating joint disease, arthritis and inflammatory conditions in afflicted mammals. The compositions of the invention are also useful in alleviating pain in mammalian subjects. The mammal may be any mammal such as a human, a domestic animal, a farm animal, such as a stud, breeder or grower animal, such as for meat or dairy production. In the treatment of clinically relevant arthritis, for example, the farm animal may be a pig. The pig may be a young pig or may be a breeder sow. For example a clinically affected pregnant sow may be treated to assist them to get through to farrowing.

Treatment of Pain

The inventor has identified that compositions of the invention are useful in the treatment of subjects having pain. Various specific types of pain are described herein, including the following.

Painful Musculoskeletal Conditions Other than Arthritis.

Painful musculoskeletal conditions are common, with a prevalence of approximately 30%. For musculoskeletal conditions other than arthritis, the prognosis is generally good; most people recover within a few weeks following the onset of symptoms. However a significant minority do not recover and develop long lasting or chronic pain, defined as pain lasting longer than 3 months. For these patients prognosis is poor and recovery is slow. A major focus of contemporary research is the early identification of patients who are at a high risk of a poor outcome. A common finding from this research is that early high pain intensity is a risk factor for delayed recovery and the development of chronic pain.

The most frequent cause of chronic musculoskeletal pain is low back pain. Over 1 million Australians have a disability associated with their back problems and it is the leading reason for Australians leaving the workforce. Other common but less prevalent chronic pain conditions include: neck and shoulder pain, whiplash associated disorder (WAD) and complex regional pain syndrome (CRPS).

Back pain is an extremely common, difficult-to-manage and expensive health condition. In Australia back pain is associated with costs of around $9 billion/year. Over 85% of low back pain is 'non-specific' low back pain (NSLBP) in that a structural source of the pain cannot be reliably identified. Plausible therapeutic targets are innervated tissues and include the disc, the facet joint and the sacroiliac joint, however other tissues such as muscle and ligament may also be involved. Up to 15% of low back pain is radiculopathy where impingement of the nerve root causes symptoms including back and leg pain. Pain associated with radiculopathy is believed to be associated with a local inflammatory process. Treatments for radicular pain include advice to stay active, analgesia including NSAIDS, epidural corticosteroid injection and transfroaminal peri-radicular injections of corticosteroid.

Neck and Shoulder Pain

Whiplash associated disorder (WAD) are injuries to the neck caused by acceleration-deceleration energy transfer resulting most commonly from a motor vehicle accident. As with most painful musculoskeletal conditions prognosis for new injuries is typically good in the first few weeks or months, but after 3 months recovery rates slow markedly and a significant proportion of patients develops chronic Whiplash Associated Disorder (WAD). High pain intensity is known to be a predictor or poor outcome. Whiplash is largely resistant to conservative treatments.

Complex Regional Pain Syndrome

Complex regional pain syndrome (CRPS) is a complication of minor trauma, usually to one limb, characterised by incapacitating pain, swelling, colour and temperature changes, and bone demineralisation in the limb. In Australia on average 5000 people are diagnosed with CRPS every year. The most common inciting minor trauma is wrist fracture. The incidence of CRPS following wrist fracture is 5-7%. Prognosis is poor and treatment options are often highly invasive, have significant side effect profiles and are only moderately effective. The major cause of CRPS is thought to be an aberrant inflammatory response to tissue injury and a more pro-inflammatory balance of inflammatory mediators is expressed by patients with CRPS compared to those without the condition.

Neuropathic Pain

The inventor has identified that compositions of the invention are useful in the treatment of subjects having pain for which there is no discernable clinical cause, such as some forms of neuropathic pain. Neuropathic pain refers to a group of painful disorders characterized by pain due to dysfunction or disease of the nervous system at a peripheral level, a central level, or both. It is a complex entity with many symptoms and signs that fluctuate in number and intensity over time. The three common components of neuropathic pain are steady and neuralgic pain; paroxysmal spontaneous attacks; and hypersensitivity.

Neuropathic pain can be very disabling, severe and intractable, causing distress and suffering for individuals, including dysaesthesia and paraesthesia. Sensory deficits, such as partial or complex loss of sensation, are also commonly seen. In addition, there are significant psychological and social consequences linked to chronic neuropathic pain, which contribute to a reduction in quality of life.

Neuropathic pain is quite common in general medical practice. In some forms, the neuropathic pain is not associated with any discernable clinical causative condition. As an example it is demonstrated herein that the compositions of the invention are effective in alleviating neuropathic facial pain. In some forms, the neuropathic pain is associated with a discernable clinical condition. The prevalence of trigeminal neuralgia is 2.1 to 4.7 persons per 100,000 of the population, and of painful diabetic neuropathy occurs in 11% to 16% of Type 1 diabetics as well as Type II diabetics and postherpetic neuralgia is found in approximately 34 persons per 100,000 of the population. Treatment of neuropathic pain is not easy. Patients with neuropathic pain do not always respond to standard analgesics such as non-steroidal anti-inflammatory drugs (NSAIDs) and to some extent neuropathic pain is resistant to opiates. The pharmacologic agents best studied and longest used for the treatment of neuropathic pain are antidepressants and anticonvulsants both of which may have serious side effects.

A composition of the invention may be administered to a subject for treatment of such pain at any appropriate site. Administration may typically be using an appropriate type of injection or it may be by topical application. For example, an injection may be subcutaneous, intramuscular, or directly into an accessible site at or near a site of the pain. As this type of pain may manifest in multiple areas of the subject's body, for example jaw pain and limb or shoulder pain, the administration may be at or near to one site of the pain and remote from another site afflicted by pain. Typically, where multiple sites of the pain occur in a patient, the administration is at or near a site identified as an original or primary site of the pain. As an illustration of this treatment, the examples herein show treatment of neuropathic facial pain by injection into the subject's gum. A subject being treated may be administered a single application of a composition of the invention, such as a single injection or may be administered multiple applications, such as multiple injections.

The invention will now be described in more detail, by way of illustration only, with respect to the following examples. The examples are intended to serve to illustrate this invention and should not be construed as limiting the generality of the disclosure of the description throughout this specification.

EXAMPLES

Example 1

Preparation of a Cell Free Extract

Preparation of Adipose Tissue

A 10 g sample of adipose tissue was collected by excision from the inguinal fat pad of a dog. The adipose tissue was rinsed with saline and then minced finely using scissors and mixed with 20 ml of Dulbecco's Modified Eagle's Medium (DMEM, Sigma). Collagenase (Sigma) was added to produce a final concentration of 0.05% w/v and the sample was incubated at 37° C. for 30 minutes. At the end of 30 minutes the adipose tissue was partially digested and consisted of a mixture of partially digested fat particles, liberated stromal vascular cells (SVCs) and liberated adipocytes. The sample was then centrifuged at 500 g for 15 minutes. Four distinct layers were visible within the centrifuged sample: a small (2 mm thick) layer of free lipid on the surface, below which was a white 20 mm thick layer of adipose tissue and adipocytes and then a large clear layer of DMEM and then a pellet of adipose tissue-derived non-adipocyte cells. The small layer of lipid was carefully removed with a pasteur pipette. A fresh pasteur, pipette was then carefully inserted through the adipocytes and the clear DMEM was removed without disturbing the floating adipose tissue, adipocytes or the pelleted cells. This resulted in a sample that contained only the floating pieces of adipose tissue and adipocytes suspended in a small volume of DMEM and the pelleted cells. The pieces of adipose tissue and adipocytes and the pelleted cells were gently mixed with a pasteur pipette and transferred to a 15 ml centrifuge tube. The pieces of adipose tissue and cells were then washed in DMEM to remove collagenase as follows. DMEM was added to a final volume of 14 ml and the sample centrifuged at 500 g for 10 minutes. This resulted in three distinct layers: floating pieces of adipose tissue and adipocytes, DMEM and pelleted adipose tissue-derived non-adipocyte cells. The DMEM was carefully removed by inserting a pasteur pipette through the adipocytes taking care not to disturb the pieces of adipose tissue, adipocytes or the pelleted cells.

Tissue Culture

The floating pieces of adipose tissue and adipocytes and the pelleted cells were gently resuspended in 10 ml of DMEM and transferred to a 300 ml tissue culture flask. A 30 ml volume of DMEM and 10 mls of autologous sterile serum were added and the flask was then incubated at 37° C. with 5% $CO_2$. The flask was examined daily by microscopy. Cells became attached and fibroblast-like in appearance between days 3 and 6. The attached cells became confluent between days 5 and 10.

Harvesting Cell Free Cell Secretions

Once cells were confluent on the base of the flask the supernatant was harvested and the suspended adipose tissue and cells were removed by filtration through a 20 micron mesh. The solution was filter sterilised through a 0.22 micron filter and then aseptically dispensed into 10 ml vials and stored frozen at −20°. In the Examples that follow, this material may be referred to as "CellFree".

Example 2

Production of Concentrated Canine Cell Free Extracts

Volumes (100 ml) of the frozen cell free extracts in Example 1 were freeze dried in a Telstar Lyobeta freeze dryer for 2 days. The resulting freeze-dried cake was rehydrated with 10 ml of distilled water. The concentrated sample was then sonicated in a sonicating water bath for 20 min. The 10 ml volumes contained a concentrated mix of cytokines.

Example 3

Subcutaneous Administration of Cell Free Extracts from Canine Adipose Tissue to Arthritic Dogs In this example the safety and efficacy of subcutaneous injections of the canine cellular secretions prepared according to Example 1 above, in the treatment of osteoarthritis in dogs was investigated. Five dogs each received subcutaneous injections in the scruff of the neck once per week for four weeks at the rate of 0.3 ml/10 kg of body weight. The dogs in this trial were predominantly advanced in age (>10 years) and had a range of joint and or bone disorders, including osteoarthritis of the elbow, chronic hip dysplasia, stifle disease and wobblers. Individually the dogs in this trial were each on a range of medications for the treatment of their conditions (Table 1). The existing medication was stopped whilst the trial was conducted. The dogs were assessed by their regular treating vets, as well as being observed by their owners for anecdotal changes, such as changes in behaviour, mobility, and obvious signs of pain. The trial is summarised in Table 1.

TABLE 1

Subcutaneous administration of cell free extracts from canine adipose tissue to arthritic dogs

| Dog/Age | Condition | Existing medication | Continued or stopped medication | Adverse effects | Comments |
| --- | --- | --- | --- | --- | --- |
| Smudge 12 y | Chronic OA of elbow | Monthly cartrophen | Stopped | None observed | OA did not deteriorate |
| Oz 14 y | Chronic hip dysplasia | Monthly cartrophen | Stopped | None observed | OA did not deteriorate |
| Daisy 13 y | Stifle disease | Metacam | Stopped | None observed | Marked improvement; less pain; more active; owners report better than Metacam |
| Lassie 10 y | Mild elbow OA | None | n/a | None observed | Moderately less lame, more mobile; less pained |
| Versace 10 y | Wobblers | Prednisone | Stopped | None observed | Large improvement in stability and activity levels |

No adverse reactions were noted with repeated injections. All five dogs did not deteriorate even though their current medications were stopped. Three of the five dogs showed significant improvement above what was seen from their previous medications.

Example 4

Subcutaneous Administration of Concentrated Secretions from Canine Adipose Tissue to Arthritic Dogs The results of the trials presented in Example 3 demonstrated that there are no adverse effects associated with the method of the invention and also demonstrated that in some treated subjects the remote administration of the adipose tissue-derived cell secretions was associated with improved activity of the subject, improved mobility or an apparently lower degree of pain. The inventor reasoned that administration of a higher dose of adipose tissue-derived cell secretions may provide further advantages.

A concentrated cell free Extract produced as described in Example 1 and 2 was used to treat 9 arthritic dogs. A 2 ml volume of the concentrated cell free, extract was administered by subcutaneous injection into the scruff of the neck. The dogs were re-examined after 10 days by a veterinarian. Results are presented in Table 2.

TABLE 2

Subcutaneous administration of concentrated secretions from canine adipose tissue to arthritic dogs

| Breed | Age (yrs) | Condition | Date treated | Outcome |
|---|---|---|---|---|
| German Shepherd | 10 | OA hips | 5 Aug. 2011 | Improved mobility and less pain. |
| Samoyed | 11 | Lameness | 19 Jul. 2011 | Improved mobility and less pain. |
| Doberman | 10 | Wobblers | 7 Jul. 2011 | Great improvement. Dog more stable, active and has greater control over bowel movements. |
| Border Collie | 12 | OA | 5 Aug. 2011 | More active, improved mobility and less pain. |
| German Shepherd | 6 | OA | 30 Jul. 2011 | Much better. More active, improved mobility and less pain. |
| Dogue de bordeaux | 3 | OA | 11 Jun. 2011 | More active, improved mobility and less pain. |
| Labrador | 12 | OA, neurological issues. | 8 Aug. 2011 | More active, improved mobility and less pain. |
| Bull mastiff cross (Chief) | 13 | Arthritic hips | 1 Apr. 2011 | More active and mobile, pain free. Effect has not waned when assessed after 5 months. |
| Golden Retriever (Ruby) | 12 | Arthritic elbows and hips | 28 Apr. 2011 | More active and mobile, pain free. Effect lasted 4 months. Effect was again apparent after re-treatment. |

Example 5

Subcutaneous Administration of Cell Free Extracts from Canine Adipose Tissue to Dogs with Atopic Dermatitis A cell free extract prepared as described in Example 1 was administered by subcutaneous injection to three dogs with atopic dermatitis. A 3 ml volume was injected into the scruff of the neck, once a week for 3 weeks. All three dogs showed an improvement when assessed by veterinary examination between 2 and 4 weeks after treatment, their condition was improved, with reduced inflammation being the primary outcome (Table 3).

TABLE 3

Subcutaneous administration of cell free extracts from canine adipose tissue to dogs with atopic dermatitis.

| Name | Age | Breed | Condition treated | Outcome | Comments |
|---|---|---|---|---|---|
| Gemma | 10 years | Bull mastiff x | Atopic dermatitis | Moderate improvement in skin condition | Generally much less inflamed, some papules still present; |
| Topaz | 6 years | German shepherd | Atopic dermatitis | Minor improvement in skin | Lesions on ventrum less inflamed, scabby tail lesion dryer. |
| BJ | 2 years | Kelpie cross | Atopic dermatitis | Significant improvement in skin condition | Feet look great, left arm lesion much improved, coat generally looks shinier. Original inflammation along ventrum, arm, chest and paws improved. |

Example 6

Subcutaneous Administration of Concentrated Cell Free Extracts from Equine Adipose Tissue in a Lame Horse An equine cell free extract was prepared as described in Example 1 using adipose tissue collected from the tail base of a horse. The adipose tissue was processed exactly as described in Example 1 except that autologous equine serum was added to the tissue culture flask instead of canine serum. The cell free extract was concentrated by freeze drying as described in Example 2.

A 2 ml volume of the concentrated cell free extract was administered by subcutaneous injection into the neck of a racehorse that was mildly lame. The horse had previously been treated with intra-articular injections of steroids and was no longer responding to this treatment.

The horse showed a marked reduction in lameness two days after administration of the cell free extract.

Example 7

Subcutaneous Administration of Concentrated Cell Free Extracts from Equine Adipose Tissue in Horses Five horses with either suspensory ligament damage or early stage osteoarthritis of the knees were treated with concentrated equine secretions (Example 6) by subcutaneous injection into the neck two days before racing. All horses demonstrated improved mobility (Table 4).

TABLE 4

Subcutaneous administration of concentrated cell free extracts from equine adipose tissue in horses

| Date | Problem | Effect |
|---|---|---|
| 16 Aug. 2011 | Early stage OA in knees | Improved mobility and less lame, performed better than expected in race. |
| 19 Aug. 2011 | Suspensory ligament injury | Improved mobility and less lame, performed better than expected in race (won). |
| 19 Aug. 2011 | Suspensory ligament injury | Improved mobility and less lame. |
| 10 Sep. 2011 | Suspensory ligament injury | Improved mobility and less lame, performed better than expected in race. |
| 10 Sep. 2011 | Early stage OA in knees | Improved mobility and less lame, performed better than expected in race. |

Example 8

Treatment of Osteoarthritis in Dogs by Subcutaneous Injection of Cryopreserved Allogeneic Adipose Derived Cells Including Adipocytes Processing of Adipose Tissue A 10 g sample of falciform adipose tissue was collected from a female dog during a routine desex procedure. The adipose tissue was rinsed with saline and then minced finely using scissors and mixed with 20 mls of Dulbecco's Modified Eagle's Medium (DMEM, Sigma). Collagenase (Sigma) was added to a final concentration of 0.05% (w/v) and the sample was incubated at 37° C. for 90 minutes. During the incubation the sample was gently inverted by hand every 15 minutes.

Following collagenase treatment the sample was aseptically filtered through a stainless steel mesh (700 micron pore size), transferred to a 50 ml centrifuge tube and centrifuged at 500 g for 15 minutes.

Four distinct layers were visible within the centrifuged sample: a small (2 mm thick) layer of free lipid on the surface, below which was a white 10 mm thick layer of adipocytes and then a large clear layer of DMEM and then a pellet of SVF cells. The small layer of oil was carefully removed with a pasteur pipette. A fresh pasteur pipette was then carefully inserted through the adipocytes and the clear DMEM was removed without disturbing the floating adipocytes or the pelleted SVF cells. This resulted in a sample that contained only the floating adipocytes and the pelleted SVF cells. The floating and the pelleted cells were gently mixed with a pasteur pipette and transferred to a 15 ml centrifuge tube.

The cells were/then washed in DMEM to remove collagenase. DMEM was added to a final volume of 14 mls and the sample centrifuged at 500 g for 10 minutes. This resulted in three distinct layers: floating adipocytes, DMEM and pelleted SVF cells. The DMEM was carefully removed by inserting a pasteur pipette through the adipocytes taking care not to disturb the adipocytes or the pelleted cells.

The floating and the pelleted cells were gently resuspended in 4 mls of DMEM and mixed with a pasteur pipette.
Expansion and Cryopreservation of Cells Aliquots (0.5 mls) of the cell suspension were transferred to a T175 tissue culture flask containing 50 mls of DMEM plus 10% canine serum and incubated in a $CO_2$ incubator at 37° C. until a confluent cell monolayer was present (6 days). The floating cells (adipocytes) still had a healthy morphology at this time.

Cells were stripped with 3 mls of TrypLE Express (Invitrogen), decanted into 50 ml centrifuge tubes and centrifuged at 500×g for 10 minutes. The floating and the pelleted cells were resuspended in 2 mls of canine serum plus 10% DMSO and transferred to a cryovial. The cryovials were frozen in a Mr Frosty slow freezing device (Invitrogen) in a −80° C. freezer for 24 hours and then transferred to a liquid nitrogen dewar.
Administration of Cells to Dogs Seven dogs with osteoarthritis were given a single subcutaneous injection of cells into the scruff of the neck. The cryovial per dog was thawed at room temperature and the cell suspension drawn up with a syringe and hypodermic needle. The entire 2 mls of cell suspension was injected.
Monitoring of Dogs Dogs were monitored over an 8 week period by their owners and were examined by a veterinarian. Six of the seven dogs showed a marked improvement in their mobility and an apparent reduction in pain. The seventh dog did not improve but did not show a negative response.

Example 9

Treatment of Osteoarthritis in Dogs by Subcutaneous Injection of Cells Mixed with Cell Secretions A vial of the cryopreserved cells as described in Example 8 was removed from liquid nitrogen and mixed with 5 mls of warm (37° C.) canine secretions prepared as in Example 1. The cells and the secretions were then drawn up into a syringe and administered subcutaneously into the scruff of a dog with arthritis. The dog responded well to the treatment and showed a rapid improvement in mobility and a reduction in pain.

Example 10

Preparation of Adipose Derived Cells that had been Premixed with Cell Secretions and then Frozen Processing of Adipose Tissue A 10 g sample of falciform adipose tissue was collected from a female dog during a routine desex procedure. The adipose tissue was rinsed with saline and then minced finely using scissors and mixed with 20 mls of Dulbecco's Modified Eagle's Medium (DMEM, Sigma). Collagenase (Sigma) was added to a final concentration of 0.05% w/v and the sample was incubated at 37° C. for 90 minutes. During the incubation the sample was gently inverted by hand every 15 minutes.

Following collagenase treatment the sample was aseptically filtered through a stainless steel mesh (700 micron pore size), transferred to a 50 ml centrifuge tube and centrifuged at 500 g for 15 minutes.

The floating cells and the supernatant were discarded and the pelleted cells were gently mixed with a pasteur pipette and transferred to a 15 ml centrifuge tube.

The cells were then washed in DMEM to remove collagenase. DMEM was added to a final volume of 14 mls and the sample centrifuged at 500 g for 10 minutes. The supernatant was discarded and the pelleted SVF cells were gently resuspended in 4 mls of DMEM and mixed with a pasteur pipette.

Expansion of Cells

Aliquots (0.5 mls) of the cell suspension were transferred to tissue culture flasks containing DMEM plus 10% canine serum and incubated in a CO2 incubator at 37° C. until a confluent cell monolayer was present (7 to 10 days). Cells were stripped with 3 mls of TrypLE Express (Invitrogen), decanted into 50 ml centrifuge tubes and centrifuged at 500×g for 10 minutes. Cells were either cryopreserved at this point, in a Mr Frosty slow freezing device as described in Example 8, or they were placed into new tissue culture flasks and passaged further until they had doubled approximately 8 or 13 times. The passaged cells were then stripped and centrifuged.

Cryopreservation of Cells

The pelleted cell samples (no passage, approx. 8 doublings and approx. 13 doublings) were each divided into two samples, one was mixed with concentrated secretions whereas the other was not. The cells were resuspended in either canine serum or a mixture of canine serum plus concentrated canine secretions that were produced according to Example 1 but that had been concentrated ten-fold by centrifuging in a 3 kDa Amicon centrifugal filter tube (Millipore). The concentrated secretions were mixed with canine serum at a ratio of either 1 to 1 or at a ratio of 1 part concentrated secretions to 10 parts serum. The cell suspension were mixed with the serum and secretions and then held at room temperature for 30 minutes to allow the secretions to interact with the cells. The cell suspensions were then transferred to cryovials in 2 ml aliquots.

DMSO was added to each cryovial to produce a final concentration of 10% and the cryovials were frozen in a Mr Frosty slow freezing device (Invitrogen) in a −80° C. freezer for 24 hours and then transferred to a liquid nitrogen dewar for long term storage.

Thawing Cryopreserved Cells and Analysis of Cell Viability

Vials were removed from liquid nitrogen and allowed to thaw at room temperature. The vials were mixed by gently inverting and then a 0.1 ml volume was removed for viability measurement. The 0.1 ml volume was placed in a flow cytometry tube and mixed with 0.9 mls of Isoflow (Beckman Coulter) that contained propidium iodide (Sigma Chemical Company, Louisville, USA) at a concentration of 10 µg/mL and Syto11 (Molecular Probes, Eugene, USA) at a concentration of 1 µg/mL. Samples were analysed on a FACSCan flow cytometer and the percentage of Syto11 positive (live cells) and propidium iodide positive (dead cells) recorded.

Culture of Cryopreserved Cells

A 1 ml volume of the thawed samples were placed into a T75 tissue culture flask with DMEM and 10% fetal calf serum and incubated at 37° C. with 5% in a $CO_2$ incubator for 5 days. Flasks were then examined each day using an inverted microscope and the percentage confluency recorded.

Samples of tissue culture media from the flasks were removed and analysed using the Bio-Plex Pro Human 27-plex cytokine, chemokine and growth factor assay (Biorad, Hercules, USA) for ILR1a, G-CSF, VEGF and IL-10. Control samples of fresh media with and without secretions were included as controls.

Assessment of Cell Viability after Cryopreservation

The viability of cells frozen with the secretions was higher than the cells frozen without secretions (Table 5).

TABLE 5

Viability of passaged (13 cell doublings) and non-passaged cells frozen with and without secretions

| Cell type | Average viability post-thawing |
| --- | --- |
| Non-passaged cells with no secretions | 66.83% |
| Non-passaged cells with secretions | 75.70% |
| Passaged cells (13 cell doublings) with no secretions | 35.95% |
| Passaged cells (13 cell doublings) with secretions | 71.6% |

Assessment of Proliferation after Freezing Using the Click-iT EDU Assay

The proliferation rates of thawed cells were assessed using the Click-iT EDU assay (Life Technologies). A volume of the thawed cell suspension that contained approximately 500,000 cells was transferred to a 6 well plate. A 2 ml volume of DMEM plus 10% canine serum was added to the well. The EDU reagent was added to the well to create a final concentration of 10 µM. The plate was incubated at 37° C. with 5% $CO_2$ in a CO2 incubator at 37° C. for 2 hours. The supernatant was collected and the adherent cells were stripped and both were combined, washed (in PBS plus 1% bovine serum albumin; Sigma) and resuspended in 100 µL of Click-iT fixative and incubated for 15 min at room temperature to fix the cells. Cells were then washed and resuspended in 100 µL of Click-iT permeabilisation agent to permeabilise cells. The cells were labelled for detection, by is incubating (30 min) in the Click-iT reaction cocktail (500 µL) containing 2.5 µL of AlexaFluor 488 Fluorescent dye. Following incubation the cells were washed in Click-iT permeabilisation and wash reagent and was analysed by flow cytometry. Cells were then analysed using a FACScan flow cytometer. Proliferating cells showed an increase in green fluorescence compared to non-proliferating cells.

The results of analysing the cells are displayed in FIG. 1. The sample that had been stored frozen as cells plus secretions showed a population of proliferating cells equal to 16.8% of the total cells. The samples that had been stored frozen as cells with no secretions showed a population of proliferating cells equal to only 1.8% of the total cells.

Recovery of Cells after Freezing

The addition of secretions to cells prior to freezing the cells improved the ability of the cells to survive the freezing process and to proliferate after thawing. Cells that had been cultured until they reached cumulative cell doublings of approximately 8 and that had been frozen with secretions were observed to attach to the tissue culture flask more rapidly and grow more rapidly than the same cells frozen without secretions. At 24 hours the cells frozen with secretions had reached 90% confluency whereas the cells frozen without secretions had reached only 60% confluency (Table 6).

TABLE 6

Assessment of cultured cells (approximately 8 cumulative cell doublings) frozen with and without secretions

| Cell type | Confluency after 24 hours in culture post-thaw |
|---|---|
| Cells frozen with no secretions | 60% |
| Cells frozen with secretions | 90% |

Comparison of Cytokines Produced from Cells Frozen with and without Secretions

Cells that had been cultured through approximately 8 cumulative cell doublings and that were frozen with secretions produced a statistically significant (two-tailed t-test) greater amount of the cytokines ILr1a, IL-6, IL-8, IL-9, IL-12, IL-13, FGF basic, TNF-a and VEGF than the same cells frozen without secretions (Table 7), upon post-thaw culturing for 5 days.

TABLE 7

Comparison of cytokines produced by cells that had been frozen with or without secretions. The numbers are the means of three replicates.

| Sample | IL-1ra | IL-6 | IL-8 | IL-9 | IL-10 | IL-12 | IL-13 | FGF basic | TNF-a | VEGF |
|---|---|---|---|---|---|---|---|---|---|---|
| Cells with secretions | 80 | 8 | 17 | 10 | 43 | 91 | 8 | 14 | 20 | 5166 |
| Cells | 20 | 0 | 0 | 0 | 18 | 38 | 3 | 0 | 1 | 988 |
| p-value | 0.005 | 0.000 | 0.006 | 0.000 | 0.115 | 0.016 | 0.039 | 0.000 | 0.001 | 0.059 |

These sets of data demonstrate that there is a beneficial effect of combining secretions with cells prior to freezing the cells. Cells that are frozen without secretions lose their ability to proliferate and to produce cytokines. Including secretions with the cells prior to freezing preserves the ability of the cells to proliferate and to produce cytokines.

Example 11

Production of Secretions from Passaged Cells and Use of the Secretions to Freeze Cells Canine adipose derived cells were isolated and cultured as described in Example 10. The cells were passaged until the cells had reached a cumulative cell doubling of approximately 13 times. The tissue culture supernatant from the cells was concentrated using a 3 kDa Amicon centrifugal filter tube (Millipore). The concentrated secretions were mixed with serum at a ratio of 1 to 1. The cells were stripped, washed and the cell pellet was resuspended in the mixture of serum and secretions and then held at room temperature for 30 minutes to allow the secretions to interact with the cells. The cell suspensions were then transferred to cryovials, mixed with 10% DMSO and frozen as described in Example 10.

Figure 2:
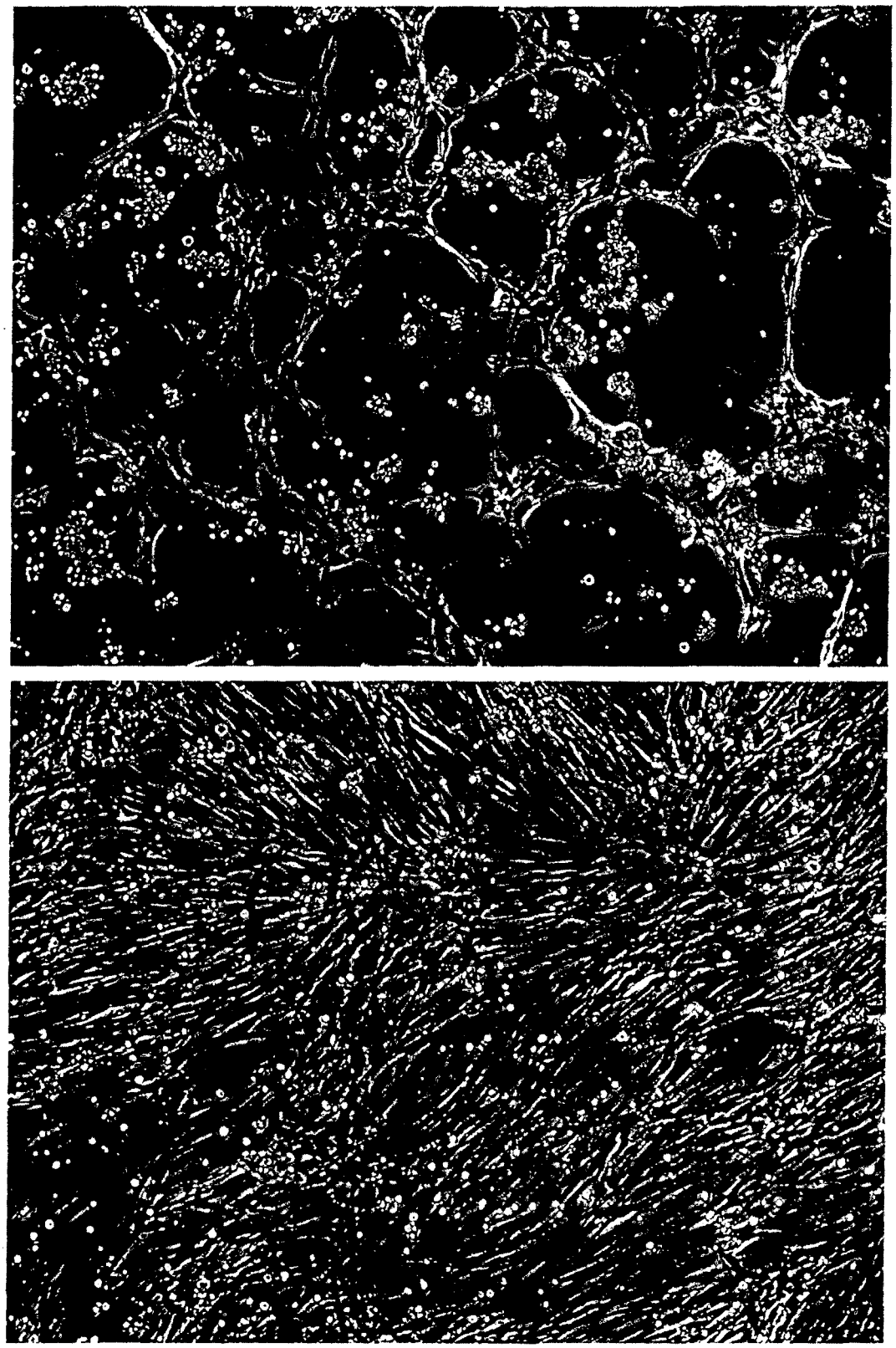
FIG. 2: Recovery of cells after freezing. Cells that had been cultured until a cumulative cell doubling of approximately 13 times had been reached were frozen without secretions (top image) and with secretions (bottom image) and then thawed and cultured for 72 hours.

The cryopreserved cell suspensions were thawed and cultured in tissue culture flasks as described in Example 10. At 72 hours the cells frozen with secretions had reached 90% confluency whereas the cells frozen without secretions had reached only 20% confluency (FIG. 2). Importantly, the cells without secretions became senescent and did not reach greater than 20% confluency even after 10 days of incubation.

This is an important finding. There is a need to be able to expand mesenchymal stem cells and other cell types in tissue culture to produce large numbers of cells. However, mesenchymal stem cells and other cell types cannot be cultured indefinitely. After a number of cell doublings the cells become senescent and will not multiply any further. This limits the number of doses that can be produced from a single culture.

To produce large numbers of cells from a single starting culture requires a cell bank of cryopreserved vials to be set up. Normally a double cell bank is created. A first set of cryopreserved vials is created and one of these vials is then thawed and used to produce a second set of cryopreserved vials. Each time a batch of product is produced one of these second set of vials is thawed and placed into culture. This cell banking process typically results in cells that are not as therapeutically effective as freshly isolated cells. By combining secretions with the cells during the freezing steps overcomes this problem and allows the production of a therapeutically effective frozen product.

Example 12

Treatment of Neuropathic Facial Pain with Autologous Adipose Derived Cells

Four human patients suffering from neuropathic facial pain were treated with an autologous adipose derived cell suspension comprised of stromal vascular fraction cells and adipocytes.

Liposuction was used to collect approximately 200 grams of adipose tissue from the abdomen and or thighs of each patient. The lipoaspirate was processed immediately after collection by washing with sterile saline and then digesting by adding sterile collagenase to a final concentration of 0.05% w/v. The sample was incubated at 37° C. for 20 minutes, filtered through a 800 micron mesh and transferred to centrifuge tubes.

The centrifuge tubes were centrifuged at 400 g for 10 minutes, and the layer between the floating adipocytes and the pelleted cells was removed. The cell pellet and floating adipocytes were combined and filter sterilized saline was added until the tubes were full. The samples were centrifuged again at 400 g for 10 minutes and the layer between the pelleted cells and the floating adipocytes was removed. The resulting cell preparation was diluted to a volume of 10 ml with sterile saline and dispensed into 2 ml volumes in sterile syringes.

The patients were given four or five injections of 2 mL volume into their gums at the original site of the pain.

Patients were followed up at between 4 and 8 weeks post treatment and their level of pain was assessed using a visual analogue scale (0=no pain, 10=worst pain imaginable). The results from these assessments are described in the Table 8 below.

TABLE 8

Administration of autologous adipose derived cells for treatment of neuropathic pain

| | Pretreatment condition | Post treatment condition |
|---|---|---|
| Patient 1 | Constant sharp neuralgic pain all day, pain in tooth and cheek, pain intensity 8. | At one month post treatment: Two or three pain episodes each day (2-3 hours each), pain in tooth only, pain intensity 6-7. |
| Patient 2 | Pain in arm, shoulder, jaw,, teeth pain intensity 9. | At two months post treatment: mild tenderness in tooth only, pain intensity 0-1. |
| Patient 3 | Pain in teeth, jaw and gum, pain intensity 8, needed Neurontin 1200 mg and Endep 50 m. | At 3 weeks post treatment: Neurontin has been reduced to 100 mg and pain in teeth and gum only, pain intensity 4. |
| Patient 4 | Facial pain intensity 8-9, only 2 hours sleep at night and woken by sharp pain. | At one month post treatment: facial pain intensity 2 but episode of higher pain intensity from cold weather, sleeps 6 hours. |

Example 13

Treatment of Pain with Topical Application of Secretions from Bovine Adipose Derived Cells A 10 g sample of adipose tissue was collected by excision from the tail-base of a 1 year old steer. The adipose tissue was rinsed with saline and then minced roughly using scissors into pieces of approximately 5 mm diameter and mixed with 20 ml of Dulbecco's Modified Eagle's Medium (DMEM, Sigma). Collagenase (Sigma) was added to produce a final concentration of 0.2% [w/v] and the sample was incubated at 37° C. for 30 minutes. At the end of 30 minutes the adipose tissue was partially digested and consisted of a mixture of partially digested fat particles, liberated stromal vascular cells (SVCs) and liberated adipocytes.

The sample was then washed to remove collagenase by centrifuging at 500 g for 15 minutes. Four distinct layers were visible within the centrifuged sample: a small (2 mm thick) layer of free lipid on the surface, below which was a white 20 mm thick layer of adipose tissue and adipocytes and then a large clear layer of DMEM/collagenase and then a pellet of adipose tissue-derived non-adipocyte cells. The small layer of lipid was carefully removed with a pasteur pipette. A fresh pasteur pipette was then carefully inserted through the adipocytes and the clear DMEM was removed without disturbing the floating adipose tissue, adipocytes or the pelleted cells. This resulted in a sample that contained only the floating pieces of adipose tissue and adipocytes suspended in a small volume of DMEM and the pelleted cells. The pieces of adipose tissue and adipocytes and the pelleted cells were gently mixed with a pasteur pipette and transferred to a 15 ml centrifuge tube.

The pieces of adipose tissue and cells were then washed in DMEM to remove collagenase as follows. DMEM was added to a final volume of 14 ml and the sample centrifuged at 500 g for 10 minutes. This resulted in three distinct layers: floating pieces of adipose tissue and adipocytes, DMEM and pelleted adipose tissue-derived non-adipocyte cells. The DMEM was carefully removed by inserting a pasteur pipette through the adipocytes taking care not to disturb the pieces of adipose tissue, adipocytes or the pelleted cells.

Tissue Culture

The floating and the pelleted cells were gently resuspended in 10 ml of DMEM and transferred to a 300 ml tissue culture flask. A 30 ml volume of DMEM and 10 mls of sterile fetal calf serum were added and the flask was then incubated at 37° C. with 5% $CO_2$. The flask was examined daily by microscopy. Cells became attached and fibroblast-like in appearance between days 3 and 6.

Harvesting Cell Free Cell Secretions

After 6 days the supernatant was harvested and the suspended adipose tissue and cells were removed by filtration through a 20 micron mesh. The solution was filter sterilised through a 0.22 micron filter and then aseptically dispensed into 10 ml vials and stored frozen at −20° C.

Preparation of Cream Containing Bovine Secretions and a Placebo Cream

A vial of the bovine secretions was thawed and mixed with an equal amount of Aqueous Base Cream BP and dispensed into plastic tubes and stored at 4° C. until used.

A second lot of cream that did not contain bovine secretions was prepared as a placebo control. DMEM was mixed with an equal amount of Aqueous Base Cream BP and dispensed into plastic tubes.

Treatment of Pain from Burns

A 46 year old male who had accidentally mildly burnt his thumb and middle finger was given a tube of each cream. The tubes were labelled as Cream 1 and Cream 2 and the man did not know which cream contained the secretions or which was the placebo. The man applied Cream 1 to the middle finger and Cream 2 to the thumb approximately 30 minutes after the burns occurred. The man reported that after 10 minutes there was no longer any pain in his thumb. The pain in the thumb did not return. The pain in the middle finger continued for approximately 6 hours. A blister formed on the middle finger but no blister occurred on the thumb.

Cream 1 was the placebo and was applied to the middle finger. Cream 2 contained the bovine secretions and was applied to the thumb.

Example 14

Intramuscular Administration of Secretions from Human Adipose-derived Cells to Mice with Collagen Antibody-induced Arthritis Preparation of Adipose Tissue Liposuction was used to collect approximately 200 grams of adipose tissue from a patient. The lipoaspirate was digested by adding sterile collagenase to a final concentration of 0.05% w/v. The sample was incubated at 37° C. for 30 minutes, filtered through a 800 micron mesh and transferred to centrifuge tubes. The tubes were centrifuged at 1500 g for 5 minutes, to obtain the pelleted cells (stromal vascular fraction; SVF) and floating adipocytes. Four distinct layers were visible within the centrifuged sample: a small layer of free lipid on the surface, below which was a thick layer of adipose tissue and adipocytes and then a large clear layer of saline and a pellet of adipose tissue-derived non-adipocyte cells (SVF). The lipid layer was aspirated and discarded. The adipocyte and SVF fractions were separately collected after the centrifugation. The fractions were washed separately with saline and centrifuged at 1500×g for 5 mins. The SVF pellet was gently resuspended in 10 mL of cell culture media that consisted of Dulbeccos Modified Eagle Medium (DMEM) supplemented with 10% foetal bovine serum and 1% penicillin-streptomycin solution.

A 300 μL portion of the SVF pellet was filtered through a 35 μm nylon mesh topped tube. A 200 μL portion of the filtered sample was enumerated and the viability determined in TruCount tubes containing isoflow, propidium iodide (10 μg/mL) and Syto11 (1 μM) using a FacsScan flow cytometer. The total number of viable nucleated cells in the SVF pellet was determined.

Tissue Culture and Harvesting of Secretions

A T175 cm$^2$ culture flask was seeded with approximately 29 million viable SVF cells and 30 mL of adipocytes. A volume of 50 mL of cell culture media, as described above, was also added to the flask. The flask was incubated at 37° C. with 5% $CO_2$ for 72 hours.

Following the 72-hour incubation, the conditioned medium was collected from the flask. This conditioned media sample was centrifuged at 4980 g for 10 mins and stored at −80° C. This conditioned media was thawed, filter sterilized using 0.22 μm syringe filter, aliquoted and frozen at −80° C. A vehicle control, containing DMEM supplemented with 1% penicillin-streptomycin solution, was also filter sterilized using a 0.22 micron syringe filter, aliquoted and frozen at −80° C. These aliquoted samples were given coded names and were shipped on dry ice to TetraQ where they were administered to mice suffering from CAIA.

Collagen Antibody-induced Arthritis Mouse Model

The collagen antibody-induced arthritis (CAIA) model is a widely accepted animal model of arthritis which has been reported in the literature to investigate the pathogenic mechanisms involved in arthritis and to screen potential therapeutic candidates. The model targets type I collagen, one of the major constituents of articular cartilage. In mice, CAIA is induced by the administration of a cocktail of 5 anti-type II collagen antibodies followed by a lipopolysaccharide (LPS) injection three days later. The subsequent administration of LPS following the antibody cocktail not only increases the severity of the arthritis through the induction of pro-inflammatory cytokines and complement component activation, but also reduces the amount of monoclonal antibody required to induce the arthritis in this model. The arthritis that develops in these mice closely resembles rheumatoid arthritis in people, including synovitis with infiltration of polymorphonuclear and mononuclear cells, pannus formation, fibrosis cartilage degradation and bone erosion. Significant swelling and redness is observed in the paws of mice suffering with CAIA. The clinical manifestations of paw redness and swelling can be assessed to assign a clinical arthritis score to mice in the CAIA model. Outcome measures of paw volume, ankle size and clinical arthritis score can be used to determine the effectiveness of a treatment on reducing the severity of arthritis in this CAIA model.

At day zero, each mouse (total of 12) received an intravenous injection of 1.5 mg (150 μL) of an anti-type II collagen 5 clone antibody cocktail. This cocktail contains 5 monoclonal antibodies: Clone A2-10 (IgG2a), F10-21 (IgG2a), D8-6 (IgG2a), D1-2G (IgG2b), and D2-112 (IgG2b) recognizing the conserved epitopes on various species of type II collagen. On day 3, mice received an intraperitoneal injection of 80 μL (40 μg/mouse) of LPS. The trial design consisted of 2 groups of 6 mice. The mice received 50 μL doses administered via the intramuscular (IM) route on days 6, 8, 10 and 12 of the following: group 1 received human secretions from the SVF+adipocytes and group 2 received the vehicle control.

The mice were monitored throughout the trial period (2 weeks) and the primary outcome measurements of paw volume, ankle size and clinical arthritis score were taken on days 0 and 2-13. The measurements were taken prior to administration of the collagen antibody cocktail (days 0) and LPS (day 3) and prior to administration of vehicle and the human SVF+adipocyte secretions. Paw volume was measured using a plethysmometer. The paw size was measured using microcalipers across the hillock (ankle joint) of each hindpaw. The mice were assessed and scored for the severity of arthritis using a standard scale (0—normal; 1—mild redness, slight swelling of ankle or wrist, redness and swelling limited to individual joints; 2—moderate swelling of ankle or wrist, redness in more than one joint, 3—severe swelling including some digits, ankle or foot; 4—maximal swelling and inflamed, involving multiple joints).

Data Analysis

The average and standard deviation (SD) of each of the primary outcome measures, paw volume (cm$^3$), ankle size (mm), and clinical arthritis score were calculated for each time-point post-treatment for both groups of mice. A two-tailed t-test was performed on the primary outcome measures at each time-point post-treatment to compare the effect of the SVF+adipocyte secretions versus the vehicle control. The statistical significance criterion was $P<0.05$.

Results

Figure 3:
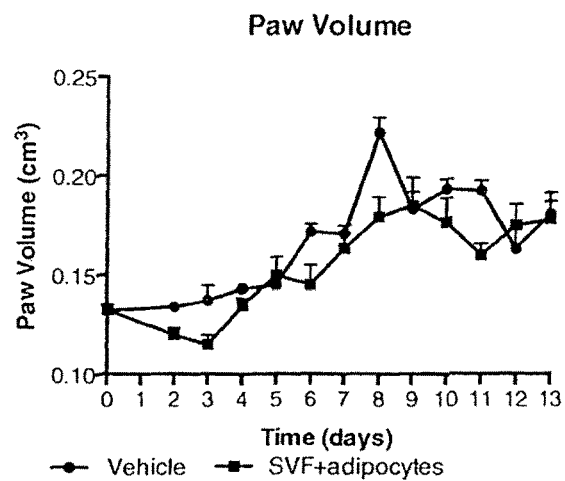
FIG. 3: Paw volume measurements from a collagen antibody induced arthritis (CAIA) mouse model treated intramuscularly with SVF+adipocyte secretions (■) or vehicle control (●).

The paw volume results for both groups are presented in FIG. 3. An analysis of the data at day 11 revealed a significant reduction (p-value=0.002) in the paw volume of mice treated with SVF+adipocyte secretions when compared to the vehicle control mice.

Figure 4:
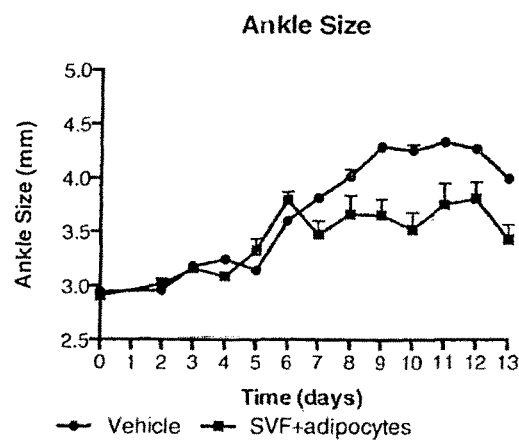
FIG. 4: Ankle size measurements from a collagen antibody induced arthritis (CAIA) mouse model treated intramuscularly with SVF+adipocyte secretions (■) or vehicle control (●).

The ankle size measurements for both groups are presented in FIG. 4. An analysis of the data at day 11 revealed a significant reduction (p-value=0.018) in the ankle size of mice treated with SVF+adipocyte secretions when compared to the vehicle control mice.

Figure 5:
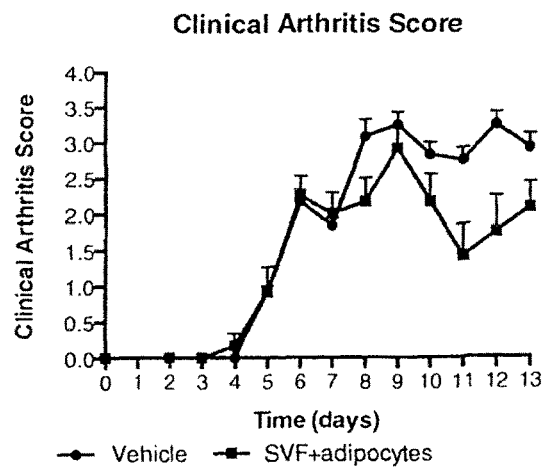
FIG. 5: Clinical arthritis scores from a collagen antibody induced arthritis (CAIA) mouse model treated intramuscularly with SVF+adipocyte secretions (■) or vehicle control (●).

The clinical arthritis scores for both treatment groups are presented in FIG. 5. An analysis of the data at day 11 revealed a significant reduction (p-value=0.017) in the clinical arthritis score of mice treated IM with SVF+adipocyte secretions when compared to the vehicle control mice.

The data clearly shows that administration of secretions by intra-muscular injection has a therapeutic effect in the CAIA mouse model. The injection site is remote from the site of the disease.

Example 15

Intravenous Administration of Adipose-derived Cells Cryopreserved in Standard Cryoprotectants Versus Cells Cryopreserved with Concentrated Secretions to Mice with Collagen Antibody-induced Arthritis Preparation of Adipose Tissue Canine adipose tissue was processed as described in Example 1 to produce canine adherent cells. Furthermore, canine secretions which were concentrated 10×, using a 3 kDa Amicon centrifugal filter tube, from adipose-derived cells, were produced as described in Example 1. From these cells and secretions, the following test products were prepared in cryovials and cryopreserved in a Mr Frosty slow freezing device (Invitrogen) in a −80° C. freezer for 24 hours and then transferred to a liquid nitrogen dewar:

1. 70,000 cells cryopreserved in 90% canine serum and 10% DMSO 2. 70,000 cells cryopreserved in 45% canine secretions (10× concentrate), 45% canine serum and 10% DMSO.

Collagen Antibody-induced Arthritis Mouse Model

The collagen antibody-induced arthritis mouse (CAIA) model described in Example 14 was also used to investigate the effects of administering the above described test products. A total of 12 mice were induced with CAIA as described in Example 14. At day 6 post-CAIA induction, the above described cryopreserved test products were thawed at room temperature immediately before injection. 6 mice were each injected intravenously with 140 µL of cells (Which equated to 70,000 cells) which had been cryopreserved in standard cryoprotectants, and the remaining 6 mice were each injected intravenously with 140 µL of cells (which equated to 70,000 cells) which had been cryopreserved in a cryoprotectant mixture which included concentrated secretions.

The mice were monitored daily throughout the trial and the primary outcome measures of paw volume, ankle size and clinical arthritis score were taken on days 0 and 2-12 as described in Example 14.

Data Analysis

The average and standard deviation (SD) of each of the primary outcome measures, paw volume ($cm^3$), ankle size (mm), and clinical arthritis score were calculated for each time-point post-treatment for both groups of mice and graphed. The delta (Δ) paw volume, ankle size and clinical arthritis score was calculated by subtracting the pre-CAIA induction score from the post-CAIA induction scores and expressing this as a percentage change. The area under the Δ paw volume, ankle size and clinical arthritis curves were determined for each group. A two-tailed t-test was used to compare the Δ paw volume, ankle size and clinical arthritis area under the curve (AUC) values from both groups.

Results

Figure 6:
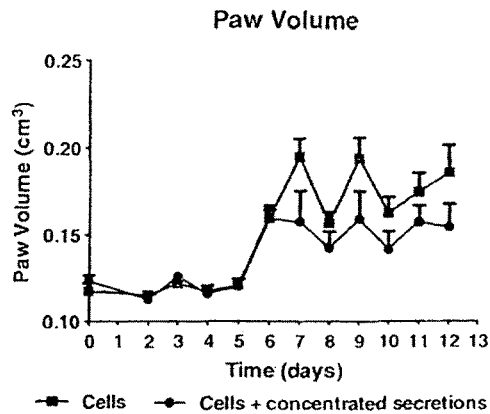
FIG. 6: Paw volume measurements from CAIA mice treated IV with cells or cells with concentrated secretions. Cells (■); cells plus secretions (●).
Figure 7:
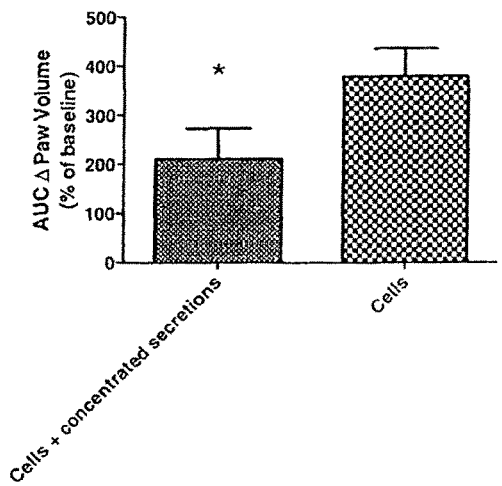
FIG. 7: Paw volume Area Under the Curve results from CAIA mice treated IV with cells or cells with concentrated secretions.

The paw volume results for both treatment groups are presented in FIG. 6. An area under the curve analysis of this data revealed a significant reduction in the paw volume of mice treated with cells and concentrated secretions when compared to cells alone (FIG. 7).

Figure 8:
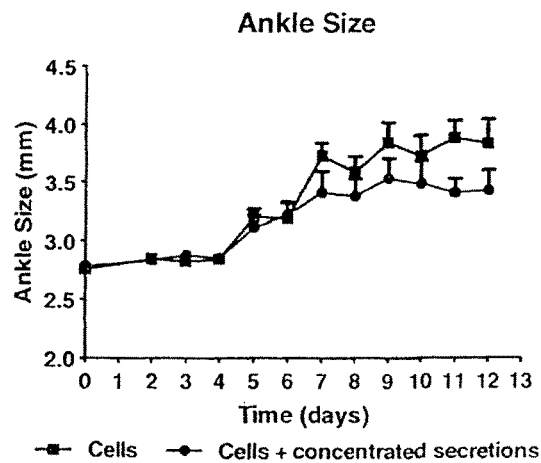
FIG. 8: Ankle size measurements from CAIA mice treated IV with cells or cells with concentrated secretions. Cells (■); cells plus secretions (●).
Figure 9:
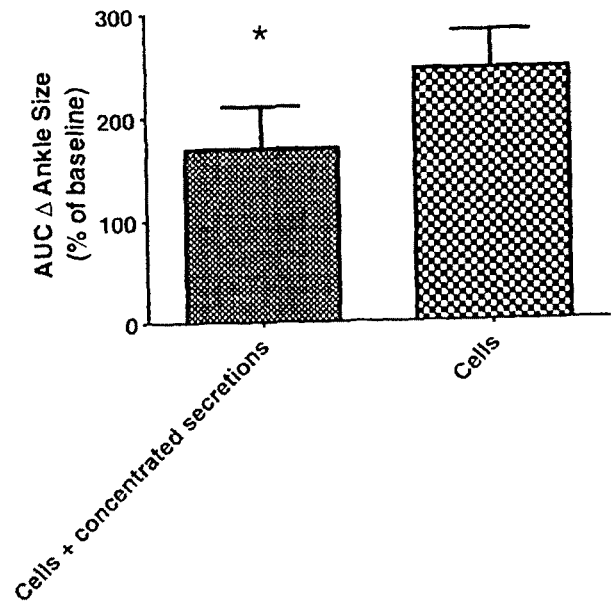
FIG. 9: Ankle size Area Under the Curve results from CAIA mice treated IV with cells or cells with concentrated secretions.

The ankle size measurements for both treatment groups are presented in FIG. 8. A significant reduction in the ankle size of mice treated with cells and concentrated secretions was observed when compared to the mice that received cells only (FIG. 9)

Figure 10:
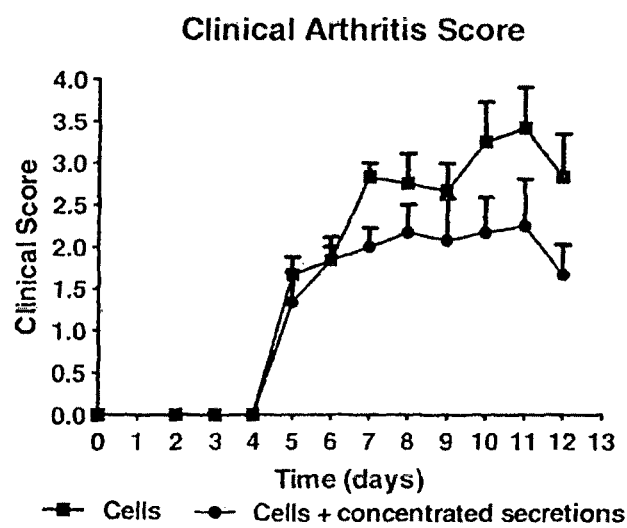
FIG. 10: Clinical arthritis scores from CAIA mice treated IV with cells or cells with concentrated secretions. Cells (■); cells plus secretions (●).
Figure 11:
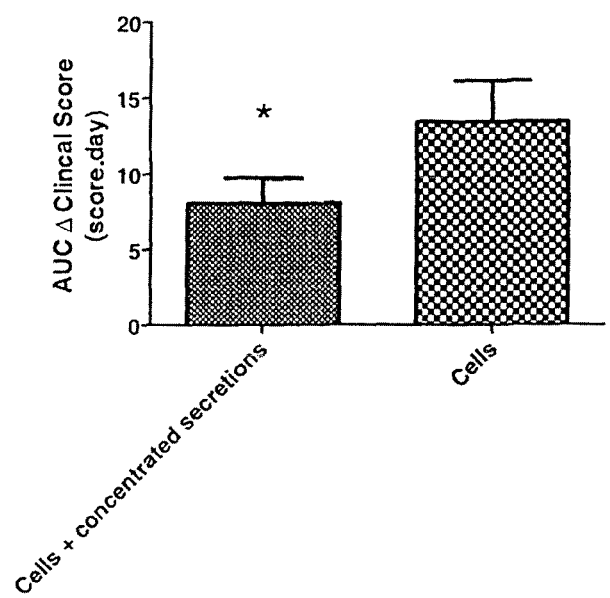
FIG. 11: Clinical arthritis score Area Under the Curve results from CAIA mice treated IV with cells or cells with concentrated secretions.

The clinical arthritis scores for both treatment groups are presented in FIG. 10. A significant reduction in the clinical arthritis score was observed in the mice treated with cells and secretions when compared to mice that received cells alone (FIG. 11).

The data shows an increased therapeutic effect by combining cells with secretions prior to freezing the cells. The data clearly shows that a frozen product that combines cells and secretions has a therapeutic effect in the CAIA mouse model. When cells alone were administered there was no therapeutic effect. This is due to the cells being damaged during the freezing process and the damaged cells are not secreting the cytokines that are required to cause the therapeutic effect. By freezing the cells with secretions the cells are able to survive the freezing process and be fully functional and capable of secreting the cytokines required to cause the therapeutic effect.

Example 16

Treatment of Pain in Dogs by Subcutaneous Administration of Adipose Derived Cells Frozen cells were prepared according to Example 10. The cell suspension was thawed and administered subcutaneously in the scruff of the neck of a dog that was suffering from sciatic nerve pain. One week after treatment the dog showed no signs of pain.

A second dog that was suffering from intervertebral disc disease and was administered a subcutaneous injection of cells in to the scuff of the neck. One week after treatment the dog showed no signs of pain.

The invention claimed is:

1. A method of alleviating pain in a mammalian subject, the method comprising,
    administering to the subject a pharmaceutical composition which comprises a combination of adipose tissue-derived cell secretions and multiply-passaged adherent cells from an adipose tissue-derived cell suspension,
    wherein said adipose tissue-derived cell secretions are prepared by culturing multiply-passaged adherent progeny cells from an adipose tissue-derived cell suspension and harvesting supernatant from the cell culture after about 3 or more days,
    said adherent progeny cells having a fibroblast-like appearance, and
    wherein said combination has been cryopreserved.

2. The method according to claim 1, wherein said administration to said subject is by intra-articular injection or by intramuscular injection or by subcutaneous injection or by topical administration.

3. The method according to claim 1, wherein the pain is back pain, or is pain associated with a burn injury, an inflammatory disorder, a ligament injury, a tendon injury, or the sciatic nerve, or is neuropathic pain.

4. The method according to claim 3, wherein the neuropathic pain is facial pain, pain of the teeth, jaw, gum or of a limb.

5. The method according to claim 1, wherein the adipose tissue-derived cell suspension (i) comprises adipocytes or (ii) is substantially free of adipocytes.

6. The method according to claim 1, wherein the subject is selected from the group consisting of (i) a human, (ii) poultry, (iii) an equine animal, (iv) a feline animal, (v) a canine animal, (vi) a bovine animal, and (vii) a porcine animal.

7. The method according to claim 1, wherein the adipose tissue-derived cell secretions or the adipose tissue-derived cell suspension is (i) derived from adipose tissue allogeneic to the recipient subject or animal, or (ii) derived from the intended recipient subject or animal, or (iii) derived from adipose tissue xenogeneic to the recipient subject or animal.

8. The method according to claim 1, wherein the adipose tissue-derived cell secretions is a preparation concentrated by between 2-fold and 20-fold.

9. The method according to claim 1, wherein said adipose tissue-derived cell secretions comprises concentrated media from culture of an adipose tissue-derived cell suspension, optionally wherein said adipose tissue-derived cell suspension (i) comprises adipocytes and adipose tissue-derived mesenchymal stem cells or (ii) is substantially free of adipocytes, optionally wherein said media from culture of an adipose tissue-derived cell suspension is concentrated between 2-fold and 20-fold.

10. The method according to claim 1, wherein the method further comprises thawing the cryopreserved combination prior to administration to the recipient subject or animal.

11. The method according to claim 10, wherein the cryopreserved combination, or pharmaceutical composition thereof, is administered to the recipient subject or animal within two hours of thawing.

12. A kit comprising (a) a pharmaceutical composition comprising a combination of adipose tissue-derived cell secretions and multiply-passaged adherent cells from an adipose tissue-derived cell suspension, wherein said adipose tissue-derived cell secretions are prepared by culturing multiply-passaged adherent progeny cells from an adipose tissue-derived cell suspension and harvesting supernatant from the cell culture after about 3 or more days, said adherent progeny cells comprising cells having a fibroblast-like appearance, wherein said combination or composition is cryopreserved; and (b) instructions for use of said kit in alleviating pain in a mammalian subject.

13. The kit according to claim 12, wherein the pain is back pain, or is pain associated with a burn injury, an inflammatory disorder, a ligament injury, a tendon injury, or the sciatic nerve, or is neuropathic pain, optionally wherein the neuropathic pain is facial pain, pain of the teeth, jaw, gum or of a limb.

14. The kit according to any claim 12, wherein the adipose tissue-derived cell suspension (i) comprises adipocytes, or (ii) is substantially free of adipocytes.

15. The kit according to claim 12, further comprising instructions for administration of said composition within 2 hours of thawing said cryopreserved composition.

16. The kit according to claim 12, wherein the adipose tissue-derived cell secretions or the adipose tissue-derived cell suspension is (i) derived from adipose tissue allogeneic to the recipient subject or animal, or (ii) derived from the intended recipient subject or animal, or (iii) derived from adipose tissue xenogeneic to the recipient subject or animal.

17. The kit according to claim 12, wherein the adipose tissue-derived cell secretions is a preparation concentrated by between 2-fold and 20-fold.

18. The kit according to claim 12, wherein said adipose tissue-derived cell secretions comprises concentrated media from culture of an adipose tissue-derived cell suspension, optionally wherein said adipose tissue-derived cell suspension (i) comprises adipocytes and adipose tissue-derived mesenchymal stem cells or (ii) is substantially free of adipocytes, optionally wherein said media from culture of an adipose tissue-derived cell suspension is concentrated between 2-fold and 20-fold.

* * * * *